(12) United States Patent
Huberman

(10) Patent No.: US 9,241,930 B2
(45) Date of Patent: Jan. 26, 2016

(54) COMPOSITIONS AND METHODS FOR TREATING VIRAL DISEASES

(75) Inventor: Eliezer Huberman, Chicago, IL (US)

(73) Assignee: NovaDrug, LLC, Chicago, IL (US)

( * ) Notice: Subject to any disclaimer, the term of this patent is extended or adjusted under 35 U.S.C. 154(b) by 0 days.

(21) Appl. No.: 14/240,583

(22) PCT Filed: Aug. 23, 2012

(86) PCT No.: PCT/US2012/052108
§ 371 (c)(1),
(2), (4) Date: Apr. 24, 2014

(87) PCT Pub. No.: WO2013/028890
PCT Pub. Date: Feb. 28, 2013

(65) Prior Publication Data
US 2014/0249178 A1    Sep. 4, 2014

Related U.S. Application Data

(60) Provisional application No. 61/526,908, filed on Aug. 24, 2011.

(51) Int. Cl.
*A61K 31/437* (2006.01)
*A61K 31/44* (2006.01)
*C07D 471/04* (2006.01)

(52) U.S. Cl.
CPC ............... *A61K 31/437* (2013.01); *A61K 31/44* (2013.01)

(58) Field of Classification Search
CPC ..... A61K 31/44; A61K 31/437; C07D 471/04
USPC .......................................... 514/300; 546/113
See application file for complete search history.

(56) References Cited

U.S. PATENT DOCUMENTS

| 5,627,165 A | 5/1997 | Glazier |
| 9,056,099 B2 * | 6/2015 | Huberman ............... 514/300 |
| 2004/0254200 A1 | 12/2004 | Davis et al. |
| 2008/0097094 A1 | 4/2008 | Schrimpf et al. |
| 2008/0207678 A1 | 8/2008 | Bondy et al. |
| 2009/0298810 A1 | 12/2009 | Busch-Petersen |

(Continued)

FOREIGN PATENT DOCUMENTS

| CN | 101619064 | 1/2010 |
| WO | WO 2007/124423 | 11/2007 |

(Continued)

OTHER PUBLICATIONS

Uchikawa; Tetrahedron Letters, 2004, 45, 9037-9040.*

(Continued)

*Primary Examiner* — Janet L Andres
*Assistant Examiner* — Daniel Carcanague
(74) *Attorney, Agent, or Firm* — Barnes & Thornburg LLP; Alice O. Martin

(57) ABSTRACT

Substituted perhydro pyrrolopyridines and methods for their use in the treatment of HIV infections, AIDS, and AIDS-related diseases, and in the treatment of BVDV infections are described herein. Also, pharmaceutical compositions comprising the substituted perhydro pyrrolopyridines are useful for the treatment of HIV infections, AIDS, and AIDS-related diseases. The compositions include one or more carriers, diluents, or excipients, or a combination thereof.

24 Claims, 10 Drawing Sheets

(56) References Cited

U.S. PATENT DOCUMENTS

| | | |
|---|---|---|
| 2010/0029706 A1 | 2/2010 | Miller et al. |
| 2013/0059881 A1* | 3/2013 | Huberman ............... 514/300 |

FOREIGN PATENT DOCUMENTS

| | | |
|---|---|---|
| WO | WO 2011/109232 | 9/2011 |
| WO | WO 2011/116287 | 9/2011 |

OTHER PUBLICATIONS

Alter; Journal of Hepatology, 2006, 44, S6-S9.*
Buckwold et al., "Bovine viral diarrhea virus as a surrogate model of hepatitis C virus for the evaluation of antiviral agents," *Antivirus Research*, 60: 1-15 (2003).
Cory et al., "Use of an aqueous soluble tetrazolium/formazan assay for cell growth assays in culture," *Cancer Commun.*, 3(7): 207-212 (1991).
Dybul et al., "Guidelines for Using Antiretroviral Agents Among HIV-Infected Adults and Adolescents—Panel on Clinical Practices for Treatment of HIV," *Ann. Intern. Med.*, 137(5 Pt 2): 381-433 (2002).
Finkielsztein et al., "What is known about the antiviral agents active against bovine viral diarrhea virus (BVDV)?," *Curr. Med. Chem.*, 17(26):2933-2955 (2010).
Hashida et al., "More reliable diagnosis of infection with human immunodeficiency virus type 1 (HIV-1) by detection of antibody IgGs to pol and gag proteins of HIV-1 and p24 antigen of HIV-1 in urine, saliva, and/or serum with highly sensitive and specific enzyme immunoassay (immune complex transfer enzyme immunoassay): A Review," *J Clin Lab Anal.*, 11: 267-86 (1997), Erratum in: *J Clin Lab Anal.*, 12(1):76 (1998).
Martinez-Picado et al. "Antiretroviral resistance during successful therapy of human immunodeficiency virus type 1 infection," *PNAS*, 97(20): 10948-10953 (2000).
Pathalk et al., "Enzymic protecting group techniques in organic synthesis," *Stereosel. Biocatal.*, 775-797 (2000).
Sepkowitz, "AIDS—the first 20 years," *N. Engl. J. Med.* 344 (23): 1764-72 (2001).
Weiss, "How does HIV cause AIDS?," *Science*, 260(5112): 1273-9 (1993).
Ago et al., "Crystal structure of the RNA_dependent RNA polymerase of hepatitis C virus," *Structure*, 7(11): 1417-1426 (1999).

Chockalignam et al., "A cell protection screen reveals potent inhibitors of multiple stages of the hepatitis C virus life cycle," *Proc. Natl. Acad. Sci. USA*, 107(8): 3764-3769 (2010).
Di Bisceglie et al., "New Therapeutic Strategies for Hepatitis C," *Hepatology*, 35(1): 224 (2002).
Gordon et al., "Control of Hepatitis C: A Medicinal Chemistry Perspective," *Journal of Medicinal Chemistry*, 48(1):1-19 (2005).
Hanazaki, "Antiviral Therapy for Chronic Hepatitis B: A Review," *Current Drug Targets—Inflammation & Allergy*, 3: 63-70 (2004).
He et al., "An intramolecular cycloaddition approach to pyrrolo[3,2-c]quinolones," *Tetrahedron Letters*, 43: 1171-1174 (2002).
He et al., "Formal total synthesis of (±)-martinellic acid," *Tetrahedron Letters*, 46: 1251-1254 (2005).
Idéo et al., "New Therapies for the Treatment of Chronic Hepatitis C," *Curr. Pharm. Des.*, 8(11): 959-966 (2002).
Kneteman et al., "Anti-HCV Therapies in Chimeric *scid*-Alb/uPA Mice Parallel Outcomes in Human Clinical Application," *Hepatology*, 43(6): 1346-1353 (2006).
Kneteman et al., "HCV796: A Selective Nonstructural Protein 5B Polymerase Inhibitor with Potent Anti-Hepatitis C Virus Activity In Vitro, in Mice with Chimeric Human Livers, and in Humans Infected with Hepatitis C Virus," *Hepatology*, 49(3): 745-752 (2009).
Lauer et al., "Hepatitis C Virus Infection," *N. Engl. J. Med.*, 345(1): 41-52 (2001).
Mercer et al., "Hepatitis C virus replication in mice with chimeric human livers," *Nat. Med.* 7(8): 927-933 (2001).
Pathalk et al., "Enzymes and protecting group chemistry," *Curr. Opn. Chem. Biol.*, 2:112-120 (1998).
Samuel, "Antiviral Actions of Interferons," *Clin. Microbiol. Rev.*, 14(4): 778-809 (2001).
Shah et al., "Synthesis and evaluation of CCR5 antagonists containing modified 4-piperidinyl-2-phenyl-1-(phenylsulfonylamino)-butane," *Bioorganic & Med. Chem. Ltrs.*, 15(4): 977-982 (2005).
Tan et al., "Hepatitis C Therapeutics: Current Status and Emerging Strategies," *Nat. Rev. Drug Disc.*, 1:867-881 (2002).
Wei et al., "New small molecule inhibitors of hepatitis C virus," *Bioorg. Med. Chem. Lett.*, 19(24): 6926-6930 (2009).
Yu et al., "Cell-based hepatitis C virus infection fluorescence resonance energy transfer (FRET) assay for antiviral compound screening," *Curr Protoc Microbiol.*, Chapter 17:Unit 17.5 (Aug. 2010).
Yu et al., "Development of a cell-based hepatitis C virus infection fluorescent resonance energy transfer assay for high-throughput antiviral compound screening" *Antimicrob. Agents Chemother.*; 53(10): 4311-4319 (2009).
Search Report and Written Opinion issued in Int'l App. No. PCT/US2012/052108 (2012).

* cited by examiner ial malformations. The economic impact of BVDV is considerable, although it is difficult to precisely estimate its level since certain infections remain undiagnosed or the losses are not recognized as being due to the virus. (see for example, Buckwold et al., Antivirus Research 2003, 60, 1; Finkielsztein et al., 2010, Current Medicinal Chemistry 17, 2933; foregoing publications, and each additional publication cited herein, are incorporated herein by reference). Thus effective therapeutics will be useful for reducing the economic impact of BDVD. Other members of this Flaviviridae family of diseases include West Nile Virus and Dengue Fever.

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcaagtgagt gcccggtt                                                   18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agctccggtt tctctttcgc t                                               21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgacttcaac agcgacaccc act                                             23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accaccctgt tgctgtagcc aaat                                            24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactagggaa cccactgctt aag                                             23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccacaaatc aaggatatct tgtc                                            24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccttggcac ttatctggga cgat                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcccagaagt tccacaatcc tcgt                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgaggattg tggaacttct ggga                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggcattgag caagctaaca gcac                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agagaaggct ttcagcccag aagt                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcactggat gcactctatc ccat                                          24

COMPOSITIONS AND METHODS FOR TREATING VIRAL DISEASES

CROSS REFERENCE TO RELATED APPLICATIONS

This application is a U.S. nationalization under 35 U.S.C. §371 of International Application No. PCT/US2012/052108, filed Aug. 23, 2012, which claims the benefit of priority under 35 U.S.C. §119(e) to U.S. Provisional Application No. 61/526,908, filed Aug. 24, 2011. The disclosures set forth in the referenced applications are incorporated herein by reference in their entireties, including all information as originally submitted to the United States Patent and Trademark Office

SEQUENCE LISTING

The instant application contains a Sequence Listing which has been submitted in ASCII format via EFS-Web and is hereby incorporated by reference in its entirety. Said ASCII copy, created on Aug. 23, 2012, is named 119221_SEQ_ST25.txt and is 2,953 bytes in size.

TECHNICAL FIELD

The invention described herein pertains to substituted perhydro pyrrolopyridines and methods for their use in treating viral infections. In particular, the invention described herein pertains to substituted perhydro pyrrolopyridines and methods for their use in treating HIV infections, AIDS, and AIDS-related diseases, and BVDV infections.

BACKGROUND AND SUMMARY OF THE INVENTION

Acquired immune deficiency syndrome (AIDS) (1) is a disease caused at least in part by the retrovirus human immunodeficiency virus (HIV) (2). AIDS and AIDS-related diseases cause a gradual decline of the immune system and leaves the HIV-infected individuals susceptible to opportunistic infections and to tumor formation that eventually leads to death. Current therapies for these diseases include antiretroviral therapy, which generally involves a cocktail of HIV protease and reverse transcriptase inhibitor drugs. It has been reported that the therapy affords a significant improvement in the general health and quality of life of many HIV-infected individuals. That recovery is also associated with a marked reduction in HIV-associated morbidity and mortality (3). Even so, the HIV protease and reverse transcriptase inhibitor drug cocktail does not cure the patient of the HIV infection nor does it prevent the return of AIDS, once the treatment is stopped. It has been reported that patients who withdraw from the therapy do not benefit from the life-saving treatment. Moreover, for a considerable fraction of AIDS patients this treatment achieves far less than optimal results due to a number of factors, including therapy intolerance, unwanted side effects, other infections, and most notably the development of drug-resistant HIV strains (4). There is a continuing need for additional treatments for AIDS, AIDS-related diseases, and HIV infections.

A member of the Flaviviridae family of positive-sense, single-stranded RNA viruses is the Bovine Viral Diarrhea Virus (BVDV). Infection with this virus brings about a severe mucosal disease in cattle and other ruminants as well as pigs. BVDV cattle infections are marked by nose, mouth and gastrointestinal mucosa ulceration, which cause continuous salivation, nasal discharge, coughing and/or diarrhea. As a result there is a quick virus spread among animals. The virus also causes calves to be still born, become persistently infected, or suffer growth retardation and/or display severe neurological malformations. The economic impact of BVDV is considerable, although it is difficult to precisely estimate its level since certain infections remain undiagnosed or the losses are not recognized as being due to the virus. (see for example, Buckwold et al., Antivirus Research 2003, 60, 1; Finkielsztein et al., 2010, Current Medicinal Chemistry 17, 2933; foregoing publications, and each additional publication cited herein, are incorporated herein by reference). Thus effective therapeutics will be useful for reducing the economic impact of BDVD. Other members of this Flaviviridae family of diseases include West Nile Virus and Dengue Fever.

It has been discovered herein that perhydro pyrrolopyridines are active anti-HIV agents. It has also been discovered herein that perhydro pyrrolopyridines are active against Flaviviridae viruses and related diseases. It has also been discovered herein that perhydro pyrrolopyridines are active anti-BVDV agents. It has also been discovered herein that perhydro pyrrolopyridines are active anti-BVDV agents. It has also been discovered herein that perhydro pyrrolopyridines are active anti-BVDV agents.

In one illustrative embodiment, described herein are substituted perhydro pyrrolopyridines that are useful for the treatment of HIV infections, AIDS, and AIDS-related diseases. In another embodiment, described herein are pharmaceutical compositions comprising the substituted perhydro pyrrolopyridines that are useful for the treatment of HIV infections, AIDS, and AIDS-related diseases. Illustratively, the compositions include one or more carriers, diluents, or excipients, or a combination thereof.

In another embodiment, described herein are methods for treating HIV infections, AIDS, and AIDS-related diseases, where the methods include administering the substituted perhydro pyrrolopyridines and/or the pharmaceutical compositions including the substituted perhydro pyrrolopyridines. In another embodiment, described herein is the use of one or more of the substituted perhydro pyrrolopyridines and/or the pharmaceutical compositions including the substituted perhydro pyrrolopyridines in the manufacture of a medicament for treating a patient or host animal having an HIV infection, AIDS, and AIDS-related diseases.

In another illustrative embodiment, described herein are substituted perhydro pyrrolopyridines that are useful for the treatment of BVDV infections. In another embodiment, described herein are pharmaceutical compositions comprising the substituted perhydro pyrrolopyridines that are useful for the treatment of BVDV infections. Illustratively, the compositions include one or more carriers, diluents, or excipients, or a combination thereof.

In another embodiment, described herein are methods for treating BVDV infections, where the methods include administering the substituted perhydro pyrrolopyridines and/or the pharmaceutical compositions including the substituted perhydro pyrrolopyridines. In another embodiment, described herein is the use of one or more of the substituted perhydro pyrrolopyridines and/or the pharmaceutical compositions including the substituted perhydro pyrrolopyridines in the manufacture of a medicament for treating a patient or host animal having a BVDV infection.

In another illustrative embodiment, described herein are substituted perhydro pyrrolopyridines that are useful for the treatment of West Nile virus infections. In another embodiment, described herein are pharmaceutical compositions comprising the substituted perhydro pyrrolopyridines that are useful for the treatment of West Nile virus infections. Illustratively, the compositions include one or more carriers, diluents, or excipients, or a combination thereof.

In another embodiment, described herein are methods for treating West Nile virus infections, where the methods include administering the substituted perhydro pyrrolopyridines and/or the pharmaceutical compositions including the substituted perhydro pyrrolopyridines. In another embodiment, described herein is the use of one or more of the substituted perhydro pyrrolopyridines and/or the pharmaceutical compositions including the substituted perhydro pyrrolopyridines in the manufacture of a medicament for treating a patient or host animal having a West Nile virus infection.

In another illustrative embodiment, described herein are substituted perhydro pyrrolopyridines that are useful for the treatment of Dengue fever. In another embodiment, described herein are pharmaceutical compositions comprising the substituted perhydro pyrrolopyridines that are useful for the treatment of Dengue fever. Illustratively, the compositions include one or more carriers, diluents, or excipients, or a combination thereof.

In another embodiment, described herein are methods for treating Dengue fever, where the methods include administering the substituted perhydro pyrrolopyridines and/or the pharmaceutical compositions including the substituted perhydro pyrrolopyridines. In another embodiment, described herein is the use of one or more of the substituted perhydro pyrrolopyridines and/or the pharmaceutical compositions including the substituted perhydro pyrrolopyridines in the manufacture of a medicament for treating a patient or host animal having a Dengue fever.

DETAILED DESCRIPTION

Figure 1:
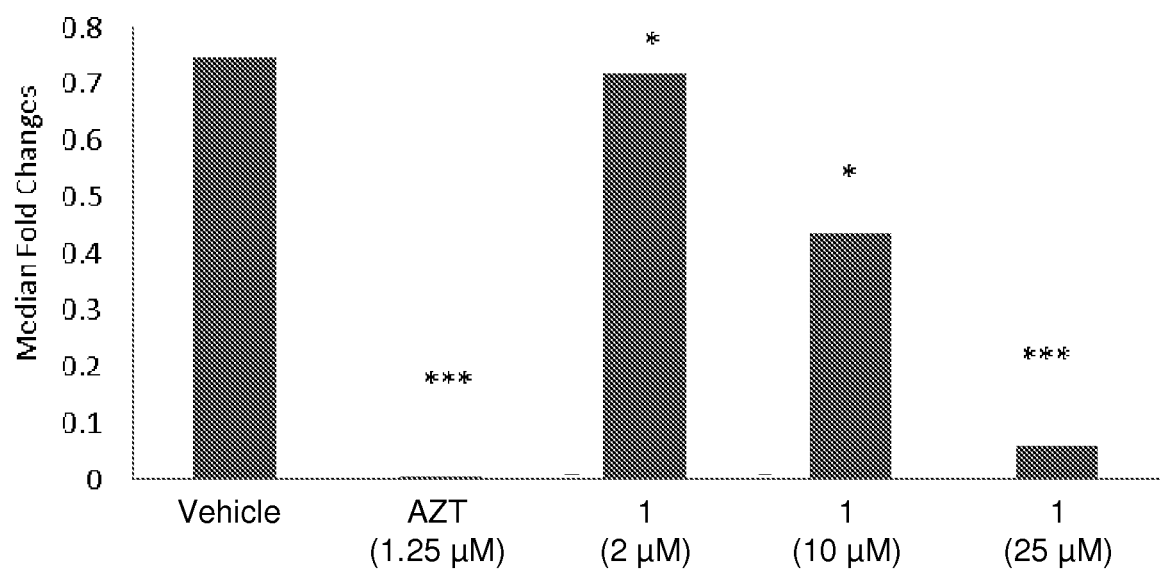
FIG. 1 shows the effect of Example 1 on HIV replication in IL-2 and phytohaemagglutinin (PHA)-stimulated cultured human peripheral blood mononuclear cells (PBMC) infected with HIV

It has been discovered herein that substituted perhydro pyrrolopyridines, including octahydro-1H-pyrrolo[3,2-c]pyridines, are useful in treating viral diseases, such as HIV infections and/or BVDV infections. Without being bound by theory, it is believed herein that substituted perhydro pyrrolopyridines decrease viral load in infected cells.

It is to be understood that as used herein, the term "perhydro pyrrolopyridines", as well as the various embodiments represented by the formulae described herein, generally refers to the parent compounds as well as pharmaceutically acceptable salts thereof, including acid and/or base addition salts. In addition, it is to be understood that the term perhydro pyrrolopyridines includes various prodrugs of the compounds, as are described herein.

In one embodiment, described herein is a compound for treating a patient or host animal having HIV, said compound of formula I

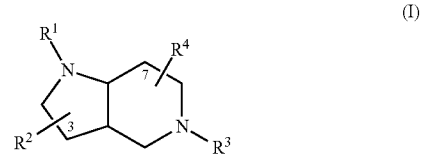

(I)

or a pharmaceutically acceptable salt thereof, wherein:
$R^1$ is arylalkyl or arylacyl, each of which is optionally substituted;
$R^2$ is hydrogen, alkyl, heteroalkyl, cycloalkyl, cycloheteroalkyl, aryl, or arylalkyl, each of which is optionally substituted;
$R^3$ is arylalkyl or arylacyl, each of which is optionally substituted; and
$R^4$ is hydrogen, alkyl, heteroalkyl, cycloalkyl, cycloheteroalkyl, aryl, or arylalkyl, each of which is optionally substituted.

In another embodiment, described herein is a pharmaceutical composition comprising the compound of formula I above, or a pharmaceutically acceptable salt thereof.

In another embodiment, the stereochemistry of the ring fusion of the compound of formula I is syn. In another embodiment, the stereochemistry of the ring fusion of the compound of formula I is as follows:

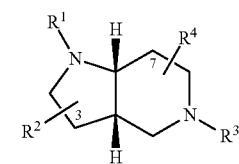

including pharmaceutically acceptable salts thereof. In another embodiment, the stereochemistry of the ring fusion and C-3 of the compound of formula I are as follows:

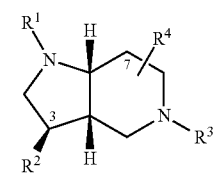

including pharmaceutically acceptable salts thereof. In another embodiment, the stereochemistry of the ring fusion of the compound of formula I is as follows:

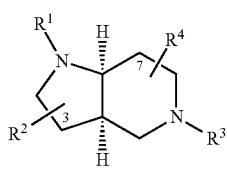

including pharmaceutically acceptable salts thereof. In another embodiment, the stereochemistry of the ring fusion and C-3 of the compound of formula I is as follows:

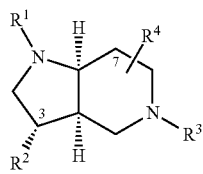

including pharmaceutically acceptable salts thereof.

In another embodiment, the substituents $R^1$, $R^2$, $R^3$, and $R^4$ of the compounds of formula I described herein, including all stereochemical variations of the compounds described herein, are each independently selected from the following hereinbelow. In another embodiment, the substituent $R^1$ of the compound of formula I described herein is optionally substituted arylacyl. In another embodiment, the substituent $R^1$ of the compound of formula I described herein is an optionally substituted arylcarbonyl. In another embodiment, the substituent $R^1$ of the compound of formula I described herein is an optionally substituted benzoyl. In another embodiment, the substituent $R^1$ of the compound of formula I described herein is benzoyl. In another embodiment, the substituent $R^1$ of the compound of formula I described herein is optionally substituted picolinoyl. In another embodiment, the substituent $R^1$ of the compound of formula I described herein is picolinoyl. In another embodiment, the substituent $R^2$ of the compound of formula I described herein is optionally substituted aryl. In another embodiment, the substituent $R^2$ of the compound of formula I described herein is optionally substituted phenyl. In another embodiment, the substituent $R^2$ of the compound of formula I described herein is phenyl substituted with halo, alkoxy, or a combination thereof. In another embodiment, the substituent $R^3$ of the compound of formula I described herein is optionally substituted arylalkyl. In another embodiment, the substituent $R^3$ of the compound of formula I described herein is optionally substituted arylmethylene. In another embodiment, the substituent $R^3$ of the compound of formula I described herein is optionally substituted benzyl. In another embodiment, the substituent $R^3$ of the compound of formula I described herein is benzyl substituted with an electron withdrawing group. In another embodiment, the substituent $R^3$ of the compound of formula I described herein is halo substituted benzyl. In another embodiment, the substituent $R^4$ of the compound of formula I described herein is hydrogen or alkyl. In another embodiment, the substituent $R^4$ of the compound of formula I described herein is hydrogen. In another embodiment, the substituent $R^2$ of the compound of formula I described herein is at C-3.

In one embodiment, described herein are pharmaceutical compositions comprising one or more of the substituted perhydro pyrrolopyridines. The substituted perhydropyrrolopyridines and the pharmaceutical compositions comprising them are useful in the treatment of HIV diseases. In another embodiment, the substituted perhydropyrrolopyridines and the pharmaceutical compositions comprising them are useful in the treatment of BVDV diseases.

In another embodiment, described herein are methods of use of the substituted perhydropyrrolopyridines and the pharmaceutical compositions comprising them for treating viral infections. Illustratively, these methods include administering to a patient or host animal in need of relief from the viral infection a therapeutically effective amount of one or more of the substituted perhydro pyrrolopyridines and/or the pharmaceutical compositions comprising them. In one variation, the methods described herein also include co-therapies with other therapeutic agents known to be useful in treating HIV. Accordingly, the compounds, compositions, formulations, uses, and methods described herein may be combined with any one or more of such compounds or agents known for treating HIV infections. Accordingly, in another embodiment, the co-therapy includes the co-administration of one or more of the compounds described herein and one or more of the known compounds or agents known to be useful in treating viral infections including HIV.

In another variation, the methods described herein also include co-therapies with other therapeutic agents known to be useful in treating BVDV, West Nile virus, and Dengue fever. Accordingly, the compounds, compositions, formulations, uses, and methods described herein may be combined with any one or more of such compounds or agents known for treating BVDV, West Nile virus, and Dengue fever infections. Accordingly, in another embodiment, the co-therapy includes the co-administration of one or more of the compounds described herein and one or more of the known compounds or agents known to be useful in treating viral infections including BVDV, West Nile virus, and Dengue fever.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl and optionally substituted heteroaryl ($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative formats for oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration.

Several illustrative embodiments of the invention are described by the following enumerated clauses:

1. A composition for treating a host animal with HIV or a related disease, BVDV, West Nile virus, or Dengue fever, or other Flaviviridae viral infection or related disease, or a combination of the foregoing, said composition comprising a compound of the formula

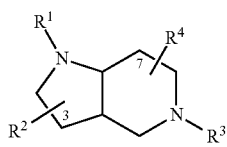

or a pharmaceutically acceptable salt thereof, wherein:
R¹ is arylalkyl or arylacyl, each of which is optionally substituted;
R² is hydrogen, alkyl, heteroalkyl, cycloalkyl, cycloheteroalkyl, aryl, or arylalkyl, each of which is optionally substituted;
R³ is arylalkyl or arylacyl, each of which is optionally substituted; and
R⁴ is hydrogen, alkyl, heteroalkyl, cycloalkyl, cycloheteroalkyl, aryl, or arylalkyl, each of which is optionally substituted.

2. The composition of clause 1 wherein the stereochemistry of the ring fusion in the compound is syn.
3. The composition of clause 1 wherein the compound is of the formula

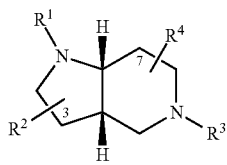

or a pharmaceutically acceptable salt thereof.
3A. The composition of clause 1 wherein the compound is of the formula

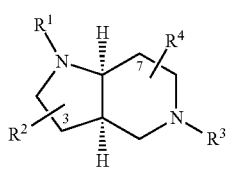

or a pharmaceutically acceptable salt thereof.
4. The composition of clause 1 wherein the compound is of the formula

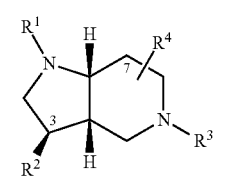

or a pharmaceutically acceptable salt thereof.

4A. The composition of clause 1 wherein the compound is of the formula

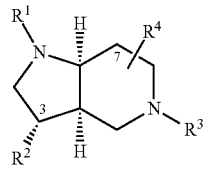

or a pharmaceutically acceptable salt thereof.
5. The composition of any one of clauses 1 to 5 wherein R¹ is optionally substituted arylacyl.
6. The composition of any one of clauses 1 to 5 wherein R¹ is optionally substituted arylcarbonyl.
7. The composition of any one of clauses 1 to 5 wherein R¹ is optionally substituted benzoyl.
8. The composition of any one of clauses 1 to 5 wherein R¹ is benzoyl.
9. The composition of any one of clauses 1 to 5 wherein R¹ is optionally substituted picolinoyl.
10. The composition of any one of clauses 1 to 5 wherein R¹ is picolinoyl.
11. The composition of any one of clauses 1 to 5 wherein R¹ is 3-picolinoyl.
12. The composition of any one of clauses 1 to 11 wherein R² is optionally substituted aryl.
13. The composition of any one of clauses 1 to 11 wherein R² is optionally substituted phenyl.
14. The composition of any one of clauses 1 to 11 wherein R² is phenyl substituted with halo, alkoxy, or a combination thereof.
15. The composition of any one of clauses 1 to 11 wherein R² is halophenyl.
16. The composition of any one of clauses 1 to 11 wherein R² is alkoxyphenyl.
17. The composition of any one of clauses 1 to 11 wherein R² is phenyl substituted with an electron donating group.
18. The composition of any one of clauses 1 to 11 wherein R² is methoxyphenyl.
19. The composition of any one of clauses 1 to 18 wherein R³ is optionally substituted arylalkyl.
20. The composition of any one of clauses 1 to 18 wherein R³ is optionally substituted arylmethylene.
21. The composition of any one of clauses 1 to 18 wherein R³ is optionally substituted benzyl.
22. The composition of any one of clauses 1 to 18 wherein R³ is benzyl substituted with an electron withdrawing group.
23. The composition of any one of clauses 1 to 18 wherein R³ is halo substituted benzyl.
24. The composition of any one of clauses 1 to 18 wherein R³ is benzyl substituted fluoro, chloro, or a combination thereof.
25. The composition of any one of clauses 1 to 18 wherein R³ is fluorobenzyl.
26. The composition of any one of clauses 1 to 18 wherein R³ is chlorobenzyl.
27. The composition of any one of clauses 1 to 26 wherein R⁴ is hydrogen or alkyl.
28. The composition of any one of clauses 1 to 26 wherein R⁴ is hydrogen.
29. The composition of any one of clauses 1 to 28 wherein R² is at C-3.

30. The composition of any one of clauses 1 to 29 for treating HIV.
31. The composition of any one of clauses 1 to 29 for treating West Nile virus.
32. The composition of any one of clauses 1 to 29 for treating Dengue fever.
33. The composition of any one of clauses 30 to 32 wherein the host animal is a human.
34. The composition of any one of clauses 1 to 29 for treating BVDV.
35. The composition of clause 34 wherein the host animal is a bovine.
36. Use of the compound of any one of clauses 1 to 29 in the manufacture of a medicament for treating a host animal with HIV.
37. A method for treating a host animal with HIV, the method comprising the step of administering to the host animal a therapeutically effective amount of one or more compounds from any one of clauses 1 to 29 alone or as a composition with one or more carriers, diluents, or excipients, or a combination thereof.
38. The method of clause 37 wherein the host animal is a human.
39. Use of the compound of any one of clauses 1 to 29 in the manufacture of a medicament for treating a host animal with BVDV.
40. A method for treating a host animal with BVDV, the method comprising the step of administering to the host animal a therapeutically effective amount of one or more compounds from any one of clauses 1 to 29 alone or as a composition with one or more carriers, diluents, or excipients, or a combination thereof.
41. The method of clause 40 wherein the host animal is a bovine.

In another embodiment, described herein is the use of one or more of the compounds described herein in the manufacture of a medicament for treating a patient or host animal having HIV, AIDS, or an AIDS-related disease, or a combination thereof.

In another embodiment, described herein is a method for treating a patient or host animal having HIV, AIDS, or an AIDS-related disease, or a combination thereof, the method comprising the step of administering to the patient or host animal a therapeutically effective amount of one or more of the compounds described herein alone or as a composition with one or more carriers, diluents, or excipients, or a combination thereof.

In another embodiment, described herein is the use of one or more of the compounds described herein in the manufacture of a medicament for treating a patient or host animal having a Flaviviridae infection or related disease.

In another embodiment, described herein is the use of one or more of the compounds described herein in the manufacture of a medicament for treating a patient or host animal having West Nile virus.

In another embodiment, described herein is the use of one or more of the compounds described herein in the manufacture of a medicament for treating a patient or host animal having Dengue fever.

In another embodiment, described herein is the use of one or more of the compounds described herein in the manufacture of a medicament for treating a patient or host animal having BVDV.

In another embodiment, described herein is a method for treating a patient or host animal having BVDV, the method comprising the step of administering to the patient or host animal a therapeutically effective amount of one or more of the compounds described herein alone or as a composition with one or more carriers, diluents, or excipients, or a combination thereof.

It is to be understood that each of the foregoing selections for $R^1$, $R^2$, $R^3$, and $R^4$ are described herein for each of the stereochemical embodiments of formula I. It is to be further understood that each of the foregoing selections for $R^1$, $R^2$, $R^3$, and $R^4$ may be combined with each other in every possible combination, each of which forms a description of a further illustrative embodiment of the invention. For example, in one such combination, described herein are compounds of formula I, including any of the stereochemical embodiments of formula I, where $R^1$ is an optionally substituted arylacyl and $R^2$ is optionally substituted aryl. In another such combination, described herein are compounds of formula I, including any of the stereochemical embodiments of formula I, where $R^1$ is an optionally substituted benzoyl; $R^2$ is optionally substituted aryl; and $R^3$ is optionally substituted arylalkyl. In another such combination, described herein are compounds of formula I, including any of the stereochemical embodiments of formula I, where $R^1$ is benzoyl; $R^2$ is optionally substituted aryl; $R^3$ is benzyl substituted with an electron withdrawing group; and $R^4$ is hydrogen.

The effective use of the compounds, compositions, and methods described herein for treating or ameliorating one or more effects of HIV, and/or BVDV using one or more compounds described herein may be based upon animal models, such as murine, canine, porcine, and non-human primate animal models of disease. For example, it is understood that HIV in humans may be characterized by a loss of function, and/or the development of symptoms, each of which may be elicited in animals, such as mice, and other surrogate test animals. Further, it is understood that BVDV in bovine may be characterized by a loss of function, and/or the development of symptoms, each of which may be elicited in alternative animals, such as mice, and other surrogate test animals. Such animal models may be used to evaluate the methods of treatment and the pharmaceutical compositions described herein to determine the therapeutically effective amounts described herein.

EXAMPLES

The following examples further illustrate specific embodiments of the invention; however, the following examples should not be interpreted in any way to limit the invention.

Example

Test Compounds. The substituted perhydropyrrolopyridines described herein are prepared using conventional processes, or are obtained from commercial suppliers (>90% purity) and used as is.

Example

Test compounds are evaluated using conventional assays for HIV infection, conventional assays for HIV protease activity, and conventional animal models of HIV disease.

Example

Blood Draw. 10 mL BD Vaccutainer, heparin coated (#367874) tubes are used to collect blood from healthy donors after consent. Average of $10 \times 10^6$ PBMCs per 10 mL tube of blood is used to determine total amount of blood drawn from each donor.

Example

Test compounds are evaluated using conventional assays for the viability of IL-2 and phytohaemagglutinin (PHA)-stimulated cultured human peripheral blood mononuclear cells (PBMC) in the presence of test compounds. Test compounds are evaluated using conventional assays on HIV replication in such cells infected with HIV. Control Cell viability is determined by a colormetric assay, such as MTS (Promega catalogue #G3582) and HIV replication by measuring the level of HIV capsid p24 antigen (5) using an ELISA kit supplied by the NIH. The substituted perhydropyrrolopyridines are dissolved in dimethyl sulfoxide (DMSO) and used at a final concentration of 25 µM. The final DMSO concentration in the growth medium is 0.5%. Azidothymidine (AZT), at a final concentration of 1 µM, serves as a positive control while DMSO in the absence of the substituted perhydropyrrolopyridines or AZT serves as a negative control.

Example

Isolation and stimulation of peripheral blood mononuclear cells (PBMCs). For the cell viability assay and P24 level assessment after substituted perhydropyrrolopyridine treatment, blood is collected from healthy consented donors using a 10 mL heparin coated tube (BD Vaccutainer #367874). The collected blood containing about $10^7$ PBMC is mixed with an equal amount of sterile phosphate buffered saline (PBS) in 50 mL tube. The blood/PBS mixture is then slowly overlaid onto 10 mL Ficoll solution (Lymphocyte separation medium) and centrifuged at 2000 rpm for 5 minutes to separate the PBMC layer from whole blood. To maintain separated layers, the centrifuge is allowed a slow stop (no brake). The PBMC are removed from the 50 mL centrifuge tube by aspiration using a sterile Pasteur pipette and placed into a 15 mL centrifuge tube to which PBS is added to fill the tube. To remove platelets, the tube is centrifuged at 2000 rpm for 5 min (with the break on) in order to pellet the freshly isolated PBMC. The supernatant with the platelets is decanted and PBS added to the tube to a 15 mL volume and centrifuged at 1400 rpm for 5 min. after which time the supernatant is decanted and the pellet suspended in 5 mL growth medium (RPMI-1640 medium plus 10% fetal bovine serum, 1% 1-glutamine and 1% penicillin/streptomycin) with 20 units/ml IL-2 and 4 ug/ml PHA and incubated for a day in T25 culture flasks at 37° C. and 5% $CO_2$ in a humidified incubator.

Example

Infection of PBMCs with HIV-1 Bal: HIV-1 Bal (NIH AIDS Research and Reference Reagent Program, Frederick, Md.) at a concentration of 2 ng virus/$10^6$ cells was added to stimulated PBMCs and incubated for 5 h at 37° C., in a 5% $CO_2$, humidified incubator. Cells were then washed with media three times. For p24 assays, $10^6$ cells per condition were resuspended in 1 mL of RPMI complete medium with 20 units/mL IL-2. Cells were left untreated or treated with 1.25 µM AZT (Sigma, St Louis, Mo.) and 1.25 µM vehicle control (DMSO). For p24 assays, infected and treated cells were then plated in a 96 well U-bottom plate at 200,000 cells in 200 µL volume of the media in quadruplicates for 6 days at 37° C., in a 5% $CO_2$, humidified incubator. For RNA isolation and subsequent real time PCR studies, $3 \times 10^6$ infected and washed cells were resuspended in RPMI complete medium with 20 units/mL of IL-2 and subjected to appropriate treatments as mentioned above and cultured at 1 mL volume in 12 well culture plates for 1 to 3 days (depending on testing time points of HIV replication cycle) at 37o° C., 5% $CO_2$ humidified incubator.

Example

HIV replication inhibition by the five substituted perhydropyrrolopyridines is determined by assaying their effect on the levels of the HIV capsid protein p24 (6) in HIV-infected PBMC. The amount of P24 is assayed by using a sandwich ELISA assay kit obtained from SAIC-Frederick AIDS (Frederick, Md.) reagent program and performed according to the manufacturer's protocol. The kit includes a coated plate, standards, primary and secondary antibodies. For this P24 determination, a day after stimulation of the PBMC with IL-2 and PHA, samples of the stimulated PBMC containing about 106 cells are centrifuged for 5 min at 2000 rpm. The supernatant is decanted and 2 ng of HIV-Bal virus stock provided by the NIH AIDS Reagent and Reference Program is added to each pellet and the cells suspended with growth medium to a total of 1 mL and incubated at 37° C. and 5% $CO_2$ in a humidified incubator. After 4 h, the cells are washed 3 times with 5 mL growth medium at 2000 rpm for 5 min. The final pellet is re-suspended in fresh growth medium to which 20 units/mL IL-2 is added. Aliquots of 1 mL PBMC suspension containing around $10^6$ cells per mL are placed into 1.5 mL microcentrifuge tubes and treated with the test chemicals. For each treatment, 4 aliquots of 200 µL (about $2 \times 10^5$ cells) are each dispensed into separate wells of a U-bottom 96 well plate and incubated at 37° C. and 5% $CO_2$ in a humidified incubator.

After 7 day incubation, the supernatant from each well is transferred to a flat bottom 96 well plate and lysed with a 1/10 volume of 10% Triton-x 100 in DI-H2O at 37° C. for 1 h. The test plates are washed three times with 200 µL of wash buffer. 100 µL of standards at 40 ng/mL, 20 ng/mL, 10 ng/mL, 5 ng/mL, 2.5 ng/mL, 1.25 ng/mL, 0.625 ng/mL, 0.3125 ng/mL, 0.1563 ng/mL and 0 ng/mL of p24 lysate control as well as 100 µL of test samples diluted 1:10 in 1% BSA, 0.2% Tween 20 in RPMI are added into the antigen-coated 96 well plate. The plates are incubated at 37° C. for 2 h and washed three times with 200 µL wash buffer. 100 µL of primary antibody solution diluted 1:150 in 10% fetal bovine serum, 2% normal mouse serum in RPMI medium is added to each well and the plates are incubated at 37° C. for 1 h. After three washes with 200 µL wash buffer, 100 µL of secondary antibody diluted 1:50 in 2% normal mouse serum, 5% NGS, 0.01% Tween 20 in RPMI medium is added. The plates are incubated at 37° C. for 1 h and washed three times with 200 µL wash buffer. 100 µL of TMB, prepared by mixing equal volumes of each component solution provided with the KPL kit (KPL, Gaithersburg, Md.), are added to each well and the plate is incubated at room temperature, in the dark for 30 min. The reaction is stopped by adding 100 µL 1N NaCl and the plates are read using a plate reader at 450 nm with a 650 nm background. A four parameter analysis is used to calculate the standard curve and concentration based on absorbance readings.

Example

Figure 3:
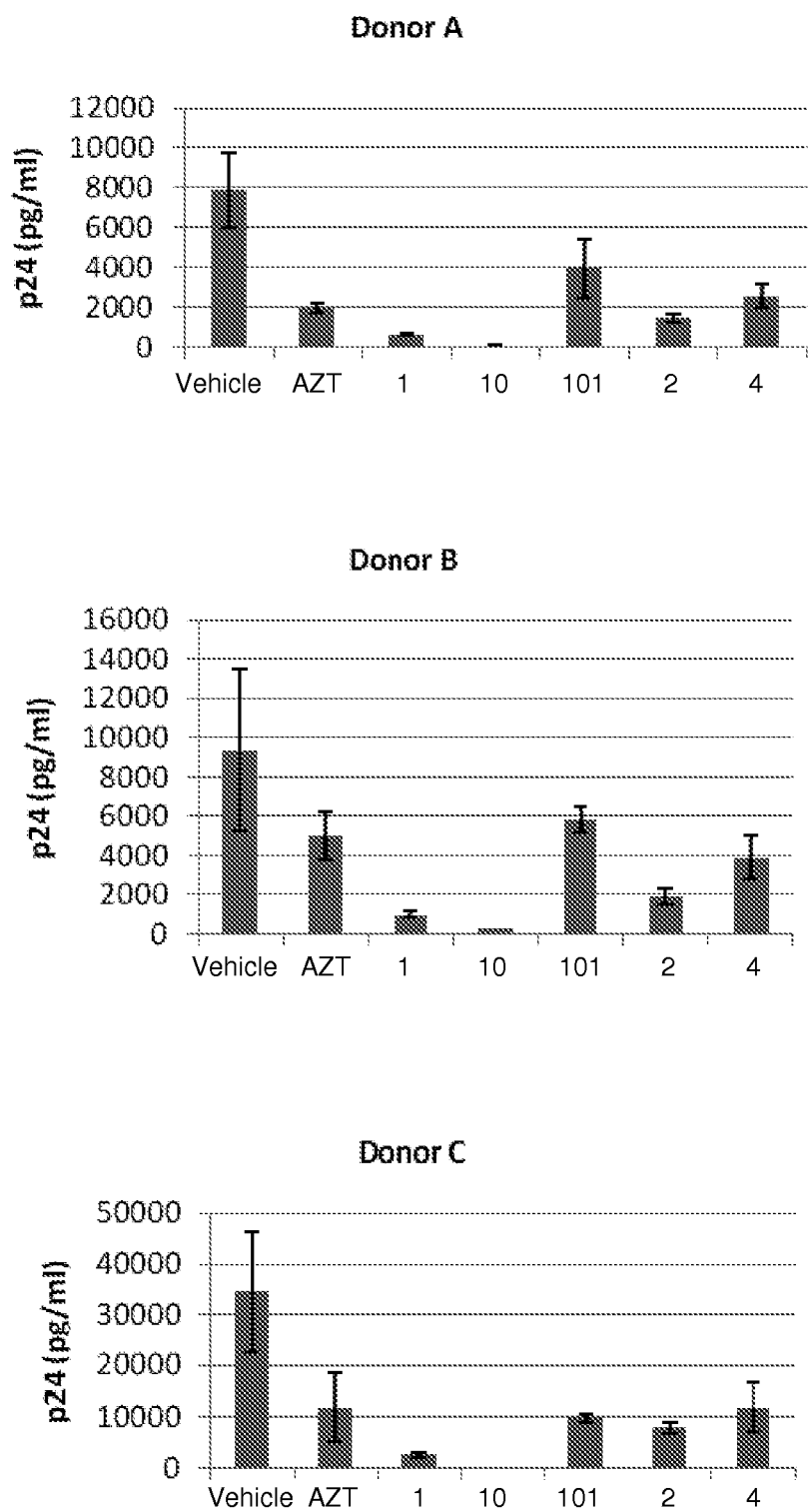
FIG. 3 shows substituted perhydropyrrolopyridine-induced reduction in p24 antigen levels in HIV-infected IL-2- and PHA-stimulated PBMC from three different consented donors.

FIG. 3 illustrates the effect of five illustrative substituted perhydropyrrolopyridines on HIV replication in IL-2 and phytohaemagglutinin (PHA)-stimulated cultured human peripheral blood mononuclear cells (PBMC) infected with HIV.

Example

FIG. 1 illustrates the effect of Example 1 on HIV replication in IL-2 and phytohaemagglutinin (PHA)-stimulated cultured human peripheral blood mononuclear cells (PBMC) infected with HIV, as a function of dose. All results represent three independent experiments performed in quadruplicates; total donors (n)=3; *=p<0.05, =p<0.001, *=p<0.0005 in comparison with vehicle (1.25 µM DMSO).

PBMCs were infected for five hours and washed three times with media. PBMCs were then treated with Example 1 at 2 µM, 10 µM, and 25 µM. HIV p24 was measured 7 days post-infection. Example 1 inhibited HIV p24 at 25 µM. PBMCs were treated with Example 1 at 2 µM, 10 µM, and 25 µM for three days. MTS assay was performed post 3 days of treatment, and readings were taken at 490 nm. Cells were viable even at the highest dosage at 25 µM.

Example

Cell viability is assayed by the "CellTiter 96® AQueous One Solution Cell Proliferation Assay" (Promega, #G3582), which assesses the metabolic activity of cells by measuring their ability to reduce MTS (3-(4,5-dimethylthiazol-2-yl)-5-(3-carboxymethoxyphenyl)-2-(4-sulfophenyl)-2H-tetrazolium in the presence of phenazine methosulfate into a formazan product that has an absorbance maximum at 490-500 nm (4). For this assay, 106 stimulated PBMC in mL of growth medium are each aliquoted into 1.5 mL microcentrifuge tubes and treated with the substituted perhydropyrrolopyridines at a final concentration of 25 µM. The control is only treated with a final concentration of 0.5% DMSO, which is the substituted perhydropyrrolopyridines solvent. After treatment, 105 PBMC in 100 µL growth medium are each inoculated into a well of a 96 well flat bottom plate with 4 replicates for the control and each of the substituted perhydropyrrolopyridines. After 6 days of incubation of the plate at 37° C. with 5% $CO_2$ in a humidified incubator treatment, 20 µL of MTS solution (Promega, #G3582) is added to each well and the plate incubated for 4 hrs at 37° C. with 5% $CO_2$ in a humidified incubator, at which time the developing color is read at an absorbance of 490 nm on a plate reader.

Example

Figure 2:
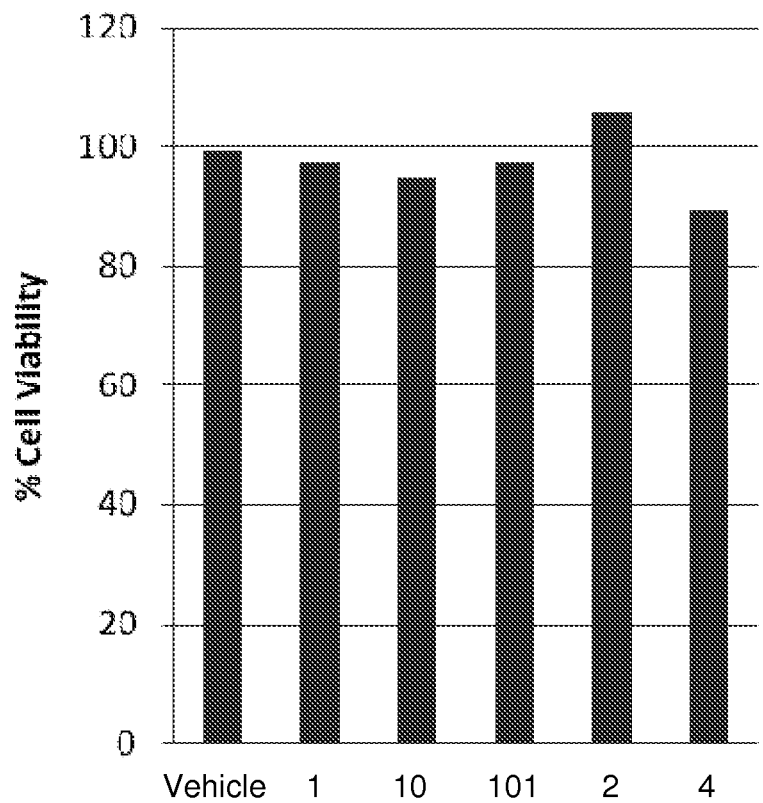
FIG. 2 shows the lack of an apparent effect of the five tested substituted perhydropyrrolopyridines on the viability of IL-2- and PHA-stimulated PBMC. The PBMC were incubated for 6 days with the substituted perhydropyrrolopyridines.

FIG. 2 illustrates the effect of five illustrative substituted perhydropyrrolopyridines on the viability of IL-2 and phytohaemagglutinin (PHA)-stimulated cultured human peripheral blood mononuclear cells (PBMC).

Example

HIV entry. For HIV entry analysis, stimulated PBMCs are pre-treated with test compounds at desired concentrations and AZT (control) for 1 h and 4 h. The PBMCs are then infected with HIV-Bal (2 ng/mL per $10^6$ cells) for 5 h. The cells are then washed with media and treated with trypsin to remove bound virus. The cells are washed two more times and RNA from samples isisolated using RNEasy MiniKit (Qiagen). DNA contamination is removed by DNaseI (Sigma) treatment at RT for 15 min followed by denaturation of DnaseI at 70° C. for 10 min. cDNA synthesis is performed using qScript cDNA supermix. Using this cDNA, real time RT-PCR is performed to quantify target genes of interest. The following primers are used to amplify HIV transcripts: HIV LTR, Forward 5'-TCAAGTGAGTGCCCGGTT (SEQ ID NO: 1) and Reverse 5'-AGCTCCGGTTTCTCTTTCGCT (SEQ ID NO: 2) and GAPDH-Forward 5'-TGACTTCAACAGCGACACCCACT (SEQ ID NO: 3) and Reverse 5'-ACCACCCTGTTGCTGTAGCCAAAT (SEQ ID NO: 4). GADPH is used as endogenous control. Example 1 did not have an effect on HIV entry.

Example

Figure 4:
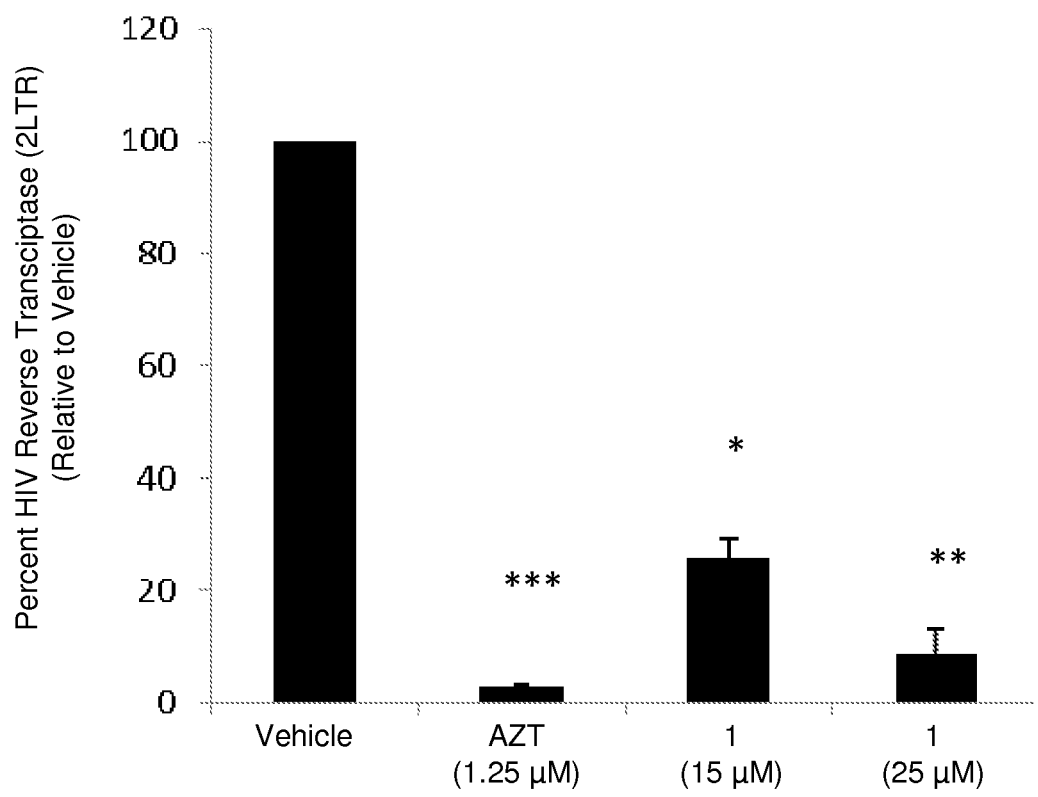
FIG. 4 shows that Example 1 significantly inhibits reverse transcription at each concentration.

HIV reverse transcription assay. Compounds described herein inhibit 2LTR circles. Stimulated PBMCs are infected with HIV-Bal (2 ng/mL per $10^6$ cells) for 5 h. PBMCs are then treated with compounds at desired concentrations and AZT (control) for 72 h post-infection. The cells are then washed three times with media and genomic DNA is prepared from samples using DNeasy Blood and Tissue Kit (Qiagen). For real time PCR analysis, the following primers are used to amplify 2LTR circles (by-products of reverse transcription): Forward 5'-AACTAGGGAACCCACTGCTTAAG (SEQ ID NO: 5) and Reverse 5'-CCCACAAATCAAGGATATCTTGTC (SEQ ID NO: 6). AZT (1.25 µM, a reverse transcriptase inhibitor) significantly inhibits HIV reverse transcription. FIG. 4 shows that Example 1 significantly inhibits reverse transcription at each concentration and appears to start to inhibit at the reverse transcription level. All results represent two independent experiments performed;*=p<0.05, =p<0.001, *=p<0.0005 in comparison with vehicle (1.25 µM DMSO).

Example

Figure 5:
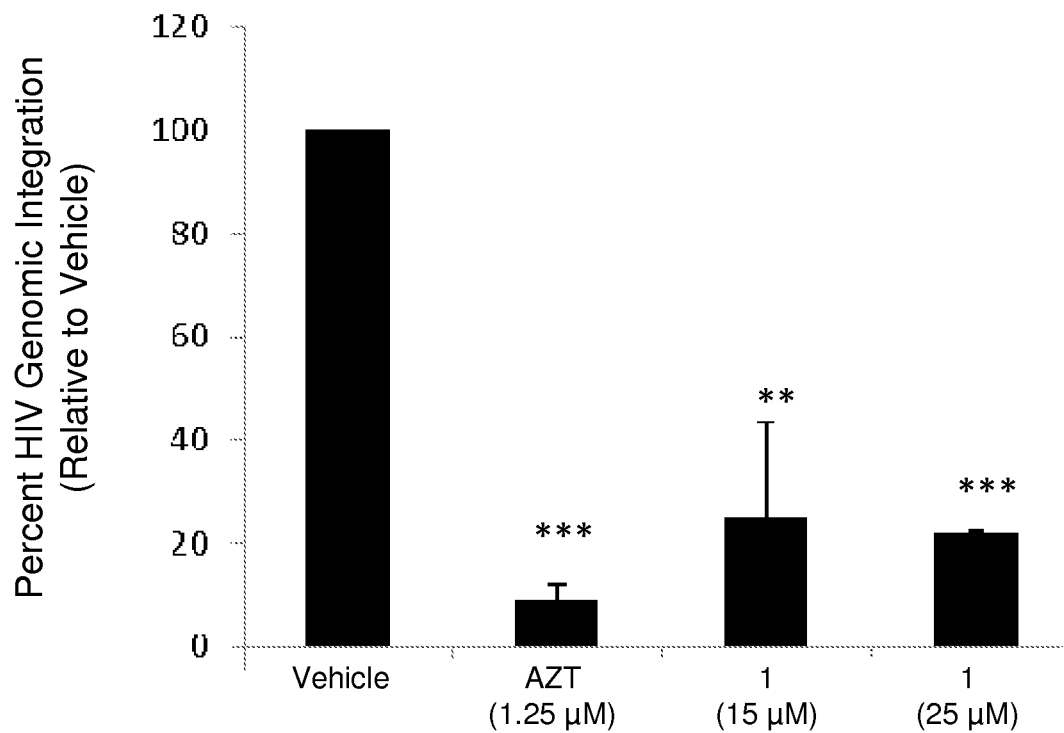
FIG. 5 shows that Example 1 significantly inhibits viral integration at each concentration.

HIV Genomic DNA Integration Compounds described herein show inhibition at the viral integration. Stimulated PBMCs are infected with HIV-Bal (2 ng/mL per $10^6$ cells) for 5 h. The PBMCs are then treated with compounds at desired concentrations and AZT (control) for 72 h post-infection. The cells are then washed three times with media. Genomic DNA is prepared from samples using DNeasy Blood and Tissue Kit (Qiagen). ALU-PCR is performed followed by real time PCR to quantify integrated viral genome. The following primers are used to amplify HIV transcripts: HIV LTR, Forward 5'-TCAAGTGAGTGCCCGGTT (SEQ ID NO: 1) and Reverse 5'-AGCTCCGGTTTCTCTTTCGCT (SEQ ID NO: 2) and GAPDH-Forward 5'-TGACTTCAACAGCGACACCCACT (SEQ ID NO: 3) and Reverse 5'-ACCACCCTGTTGCTGTAGCCAAAT (SEQ ID NO: 4). GADPH is used as endogenous control. AZT (1.25 µM, a reverse transcriptase inhibitor) significantly inhibits HIV viral integration. FIG. 5 shows that Example 1 significantly inhibits viral integration at each concentration. All results represent two independent experiments performed;*=p<0.05, =p<0.001, *=p<0.0005 in comparison with vehicle (1.25 µM DMSO).

Example

Figure 6A:
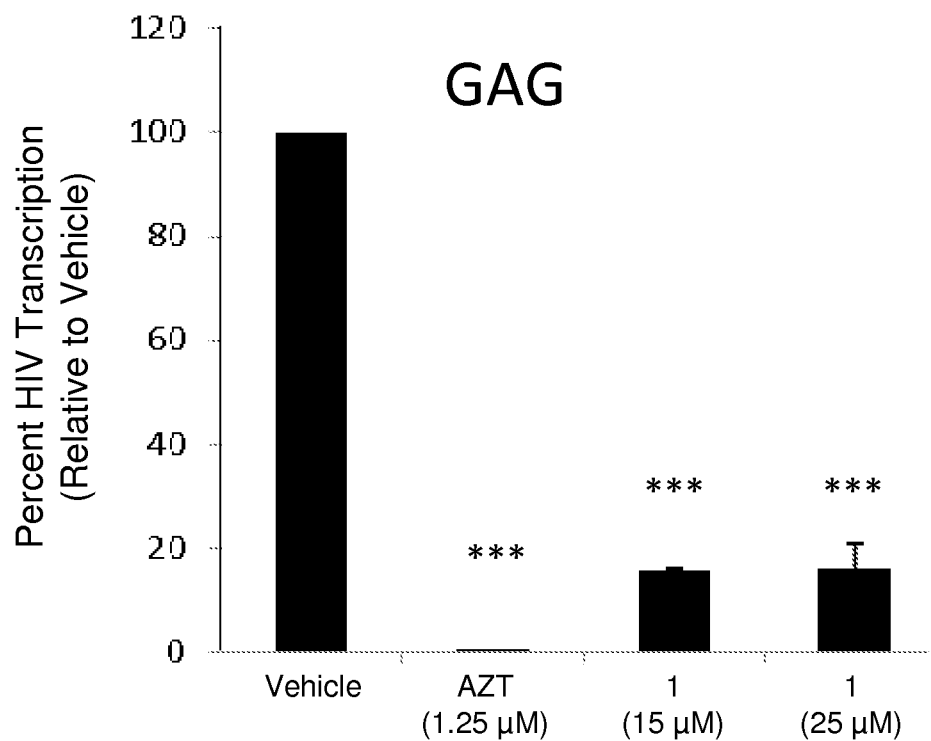
FIGS. 6A-C show that Example 1 significantly inhibits viral transcription at each concentration.
Figure 6B:
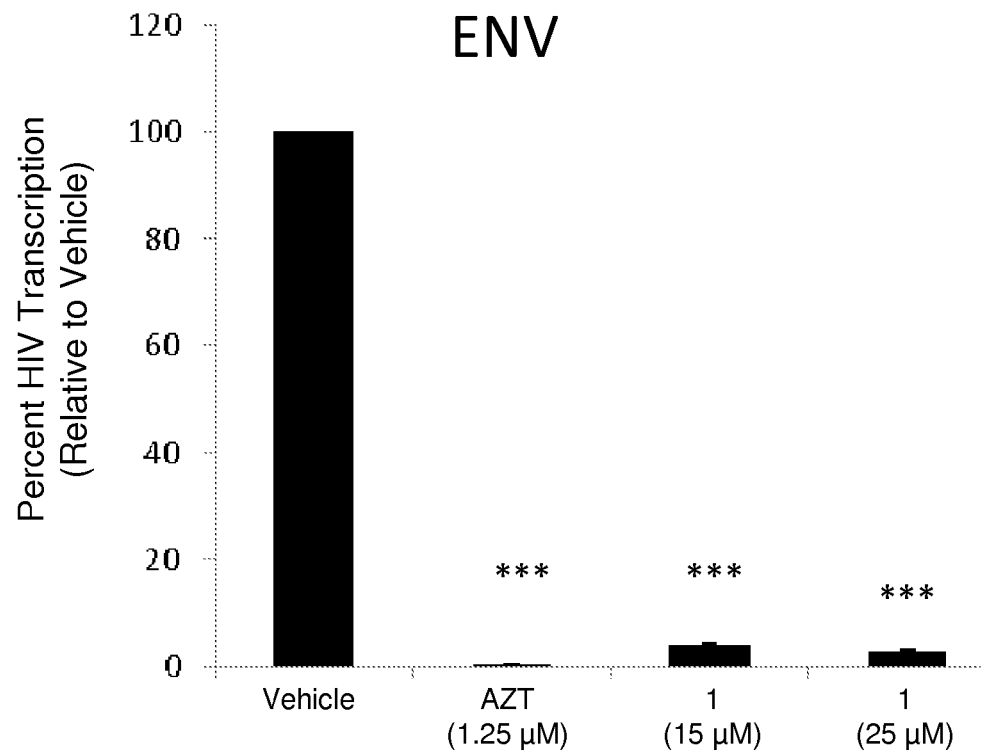
Figure 6C:
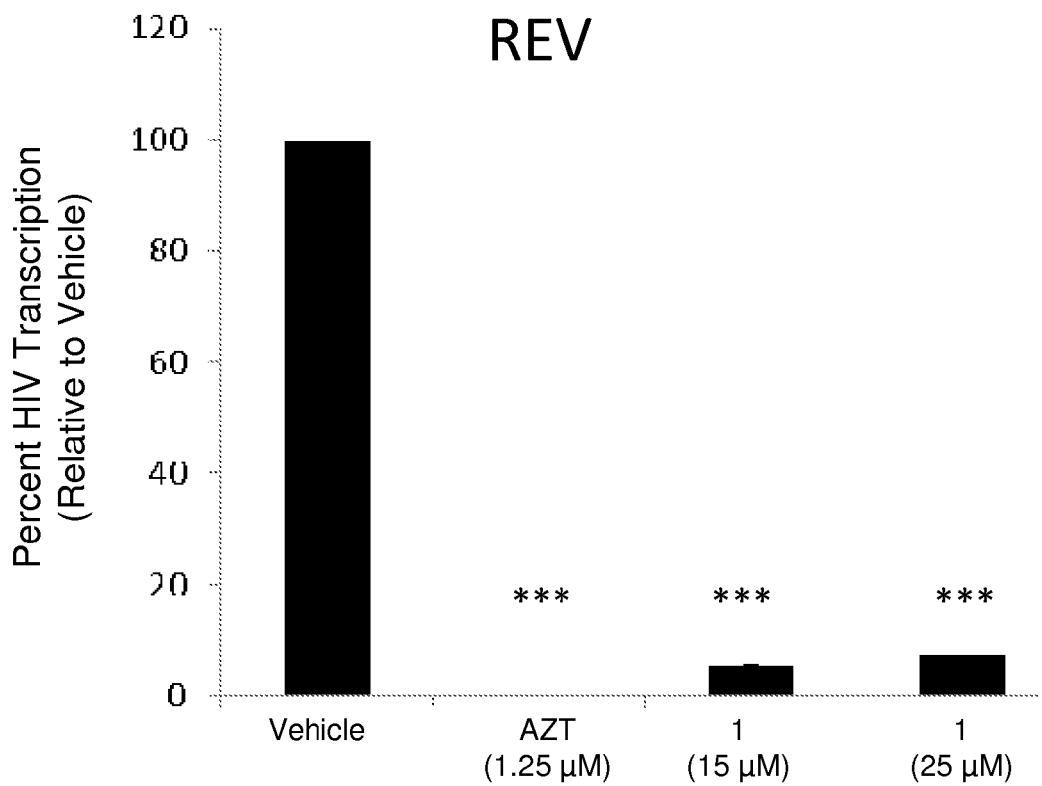

HIV transcription. Compounds inhibit at the viral transcription level. Stimulated PBMCs are infected with HIV-Bal (2 ng/mL per $10^6$ cells) for 4-6 h. PBMCs are then treated with compounds at desired concentrations and AZT (control) for 72 h post-infection. The cells are then washed three times with media and genomic RNA is prepared from samples using RNEasy MiniKit (Qiagen). Real time RT-PCR is performed to detect mature viral early (Rev) and late transcripts (Gag and Env). The following primers are used to amplify HIV transcripts: Rev, Forward 5'-TCCTTGGCACTTATCTGGGACGAT (SEQ ID NO: 7) and Reverse 5'-TCCCAGAAGTTCCACAATCCTCGT (SEQ ID NO: 8); Env, Forward 5'-ACGAGGATTGTGGAACTTCTGGGA (SEQ ID NO: 9) and Reverse 5'-TGGCATTGAGCAAGCTAACAGCAC (SEQ ID NO: 10); Gag, Forward 5'-AGAGAAG- GCTTTCAGCCCAGAAGT (SEQ ID NO: 11) and Reverse 5'-TGCACTGGATGCACTCTATCCCAT (SEQ ID NO: 12); GAPDH, Forward 5'-TGACTTCAACAGCGACACCCACT (SEQ ID NO: 3) and Reverse 5'-ACCACCCTGTTGCTG-TAGCCAAAT (SEQ ID NO: 4). GADPH is used as endogenous control. AZT (1.25 µM, a reverse transcriptase inhibitor) significantly inhibits HIV transcription. FIG. 6 shows that Example 1 significantly inhibits viral transcription at each concentration. All results represent two independent experiments performed; ***=p<0.0005 in comparison with vehicle (1.25 µM DMSO).

Example

Assay for Anti-BVDV efficacy. Cells: Bovine Turbinate (BT) cells maintained as monolayers in disposable cell culture labware are used for the antiviral efficacy test. Prior to testing, host cell cultures are seeded onto the 96-well cell culture plates and used approximately 48 hours after seeding. Cells are cultured to achieve monolayers of 80-90% confluence. The growth medium (GM) and maintenance medium (MM) include Dulbecco's Modified Eagle Media (DMEM) with L-glutamine (ATCC #30-2002), 10% Horse serum and penicillin/streptomycin (10,000 units of penicillin and 10,000 µg of streptomycin per mL, Life Technologies #15140-122 or similar) for a final concentration of 100 units penicillin and 100 µg streptomycin in the medium.

Example

Bovine Viral Diarrhea Virus strain NADL from BSLI hightiter virus stock is used. Prior to use, aliquots of the stock virus are removed and thawed from a −70° C. freezer. The BVDV is diluted in a maintenance medium (MM) to obtain 0.1 Multiplicity of Infection (MOI).

Example

Figure 7:
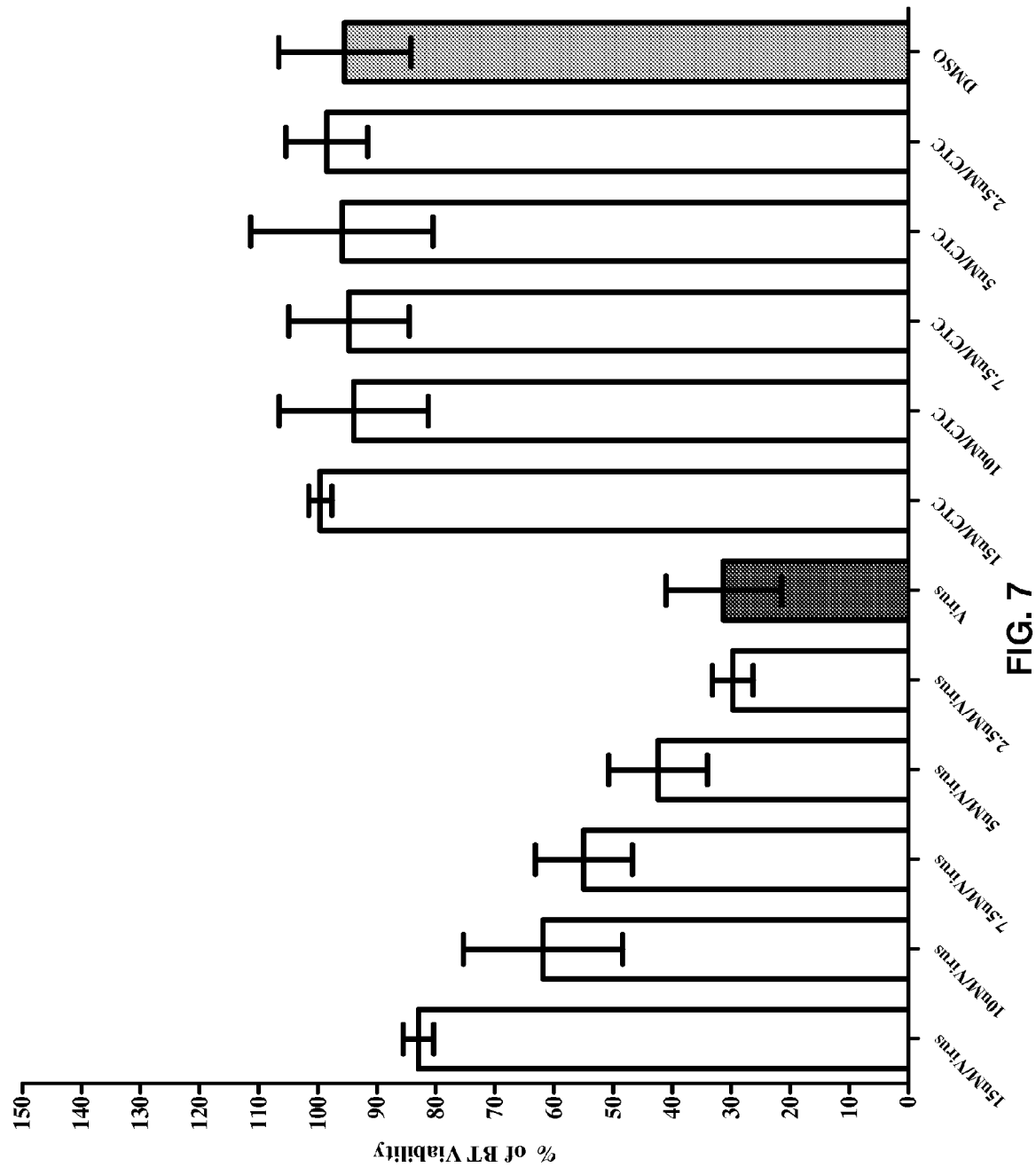
FIG. 7 shows the efficacy of Example 1 on BVDV and the lack of apparent cytotoxicity in BT cells.
Figure 8:
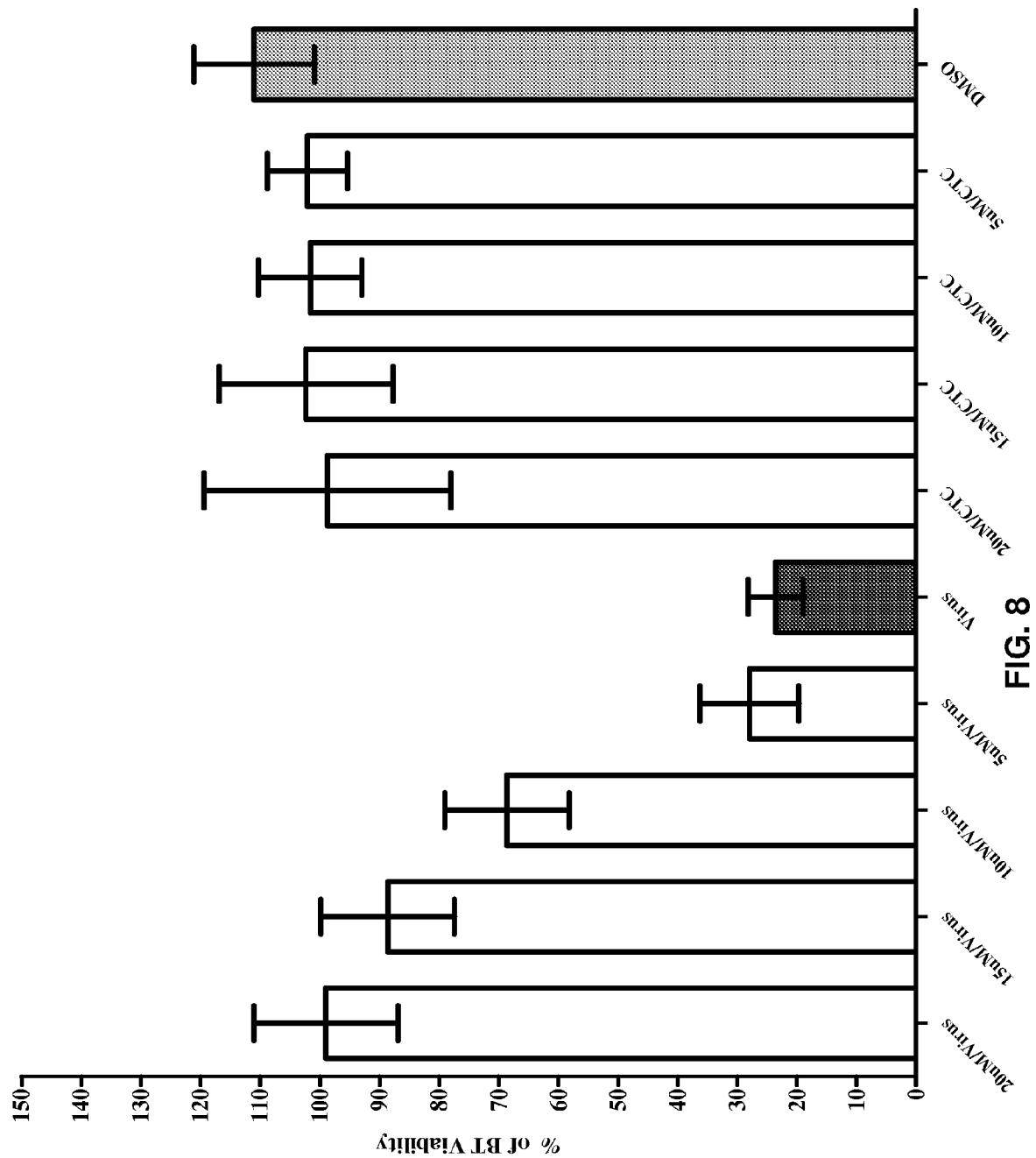
FIG. 8 shows the efficacy of Example 4 on BVDV and the lack of apparent cytotoxicity in BT cells.
Figure 9:
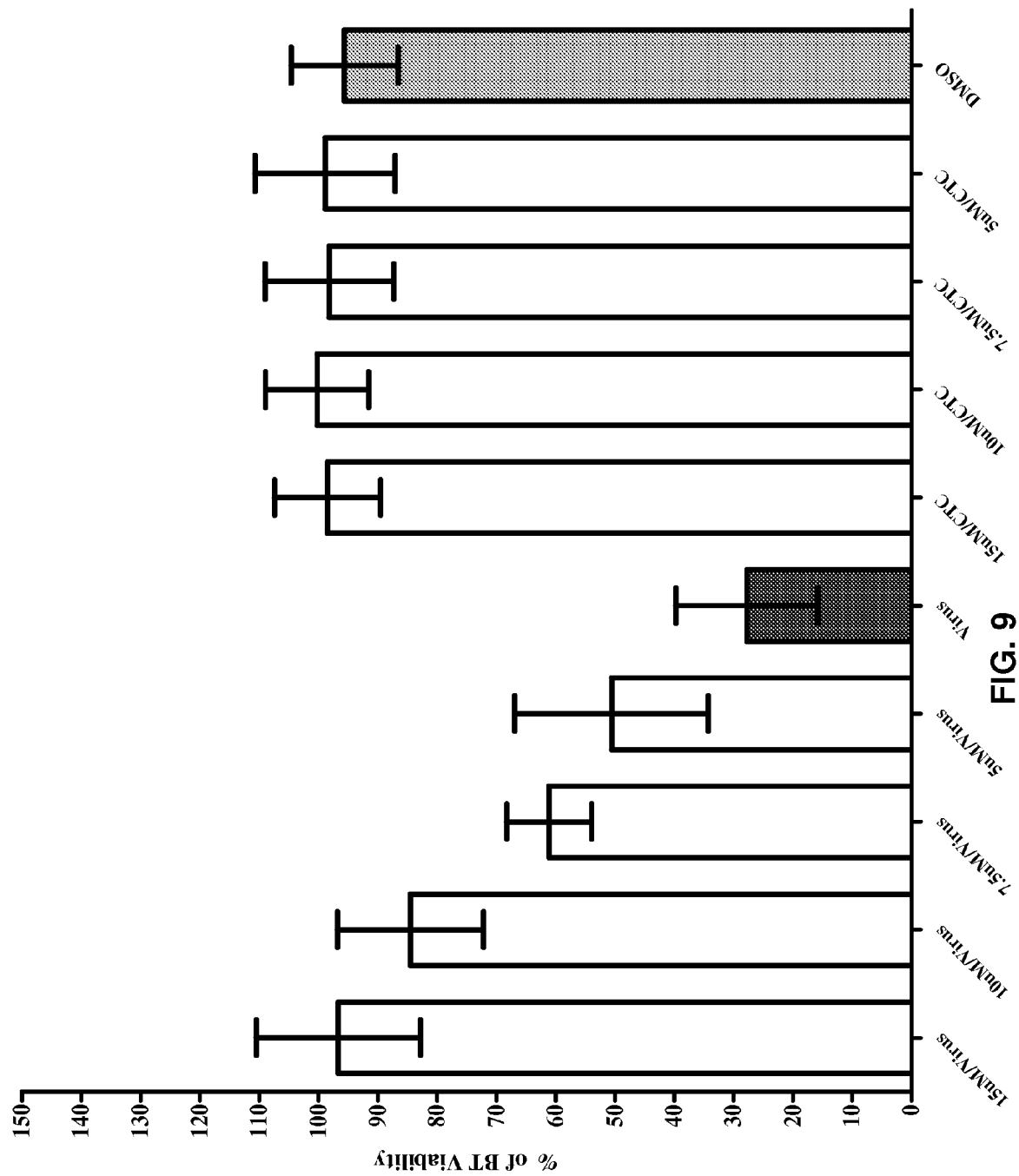
FIG. 9 shows the efficacy of Example 10 on BVDV and the lack of apparent cytotoxicity in BT cells.
Figure 10:
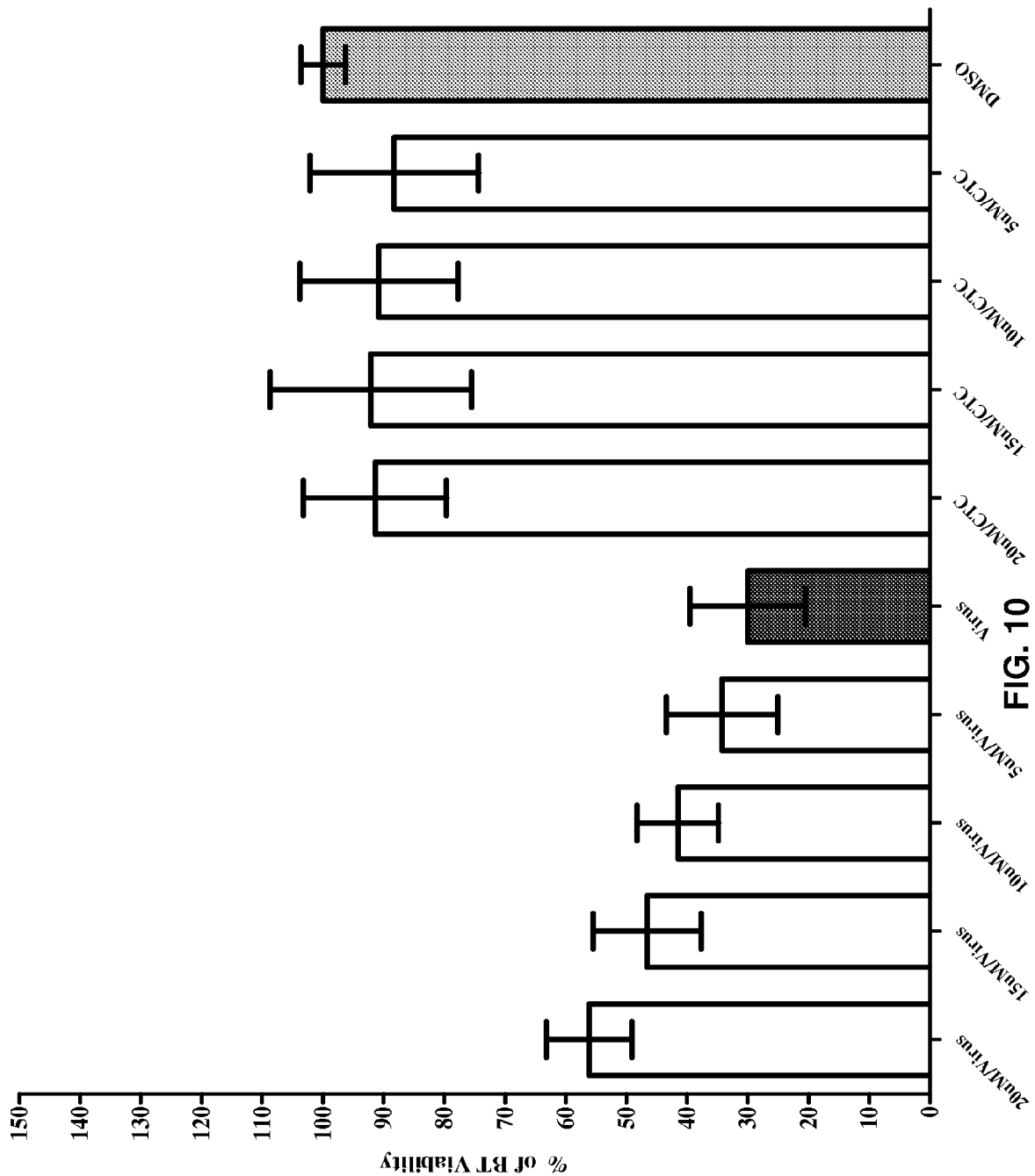
FIG. 10 shows the efficacy of Example 101 on BVDV and the lack of apparent cytotoxicity in BT cells.

Cytopathic (CPE) assay. CPE refers to degenerative changes in BT tissue culture induced by BVDV as a consequence of its multiplication. BT cell cultures are washed with PBS, and 100 µL aliquots of MM are added to the cells and incubated in a $CO_2$ incubator for 2 hours. After incubation, the MM is removed; the cells washed again with PBS and overlaid with 100 µL of the different concentrations of the tested compounds. The plates are incubated in a $CO_2$ incubator for 48 to 72 hours. Upon completion of incubation, the plates are evaluated for test compound-induced inhibition of CPE using the 3-(4,5-Dimethylthiazol-2-yl)-2,5-diphenyltetrazolium bromide, a yellow tetrazole (MTT) assay. This assay is a colorimetric assay that measures the activity of enzymes that reduce MTT to the purple color formazan dye. CPE is confirmed using an Inverted Compound Microscope. FIG. 7 shows the efficacy of Example 1 on BVDV and the lack of apparent cytotoxicity in BT cells. FIG. 8 shows the efficacy of Example 4 on BVDV and the lack of apparent cytotoxicity in BT cells. FIG. 9 shows the efficacy of Example 10 on BVDV and the lack of apparent cytotoxicity in BT cells. FIG. 10 shows the efficacy of Example 101 on BVDV and the lack of apparent cytotoxicity in BT cells. Illustrative data are shown in the following table.

| Example | IC50 (µM) | 95% CI | IC90 (µM) | 95% CI |
|---|---|---|---|---|
| 1 | 6.2 | 5.9-6.6 | 33.5 | 27.4-40.9 |
| 4 | 7.3 | 6.9-7.6 | 17.0 | 15.5-18.6 |
| 10 | 4.9 | 4.2-5.7 | 19.6 | 14.1-27.1 |
| 101 | 15.9 | 14.0-18.2 | 564.8 | 234.7-1359 |

Prior to the CPE assays, test compounds are tested to determine the highest non-cytotoxic concentration. Cell cultures are washed with PBS, overlaid with 100 µL of MM and incubated for 2 hours. After incubation, the MM is replaced with 100 µL aliquots of the test compounds at different concentrations. The cytotoxicity test includes a DMSO control (dose not to exceed 0.5%). The plates are incubated in a $CO_2$ incubator for 48 to 72 hours. Toxicity is evaluated using the MTT assay. The tests and assays are performed twice in duplicates. Results showing a significant difference are repeated two more times.

Method Example

The following protocol is used for the evaluation of PK parameters and tolerance of the animals for the test compound. The protocol includes three escalating dose levels for each of the compounds administered at a volume of 5 mL/kg once a day by intra-peritoneal (IP) injection. The tolerance is determined over a fourteen day treatment course. The study animals include three 5-mouse groups. Also included is one 5-mouse control group injected with 5 mL/kg of a vehicle. The mouse groups include both male and female 3-month old mice, such as murine KMT Mice™, with a weight range of ≥12.0 g. Blood samples are drawn via the central tail artery of the animal for measurement of serum concentrations of the substituted perhydro pyrrolopyridines on the morning of Day 8 immediately prior to the compound dose (trough sample 24 hours post the Day 7 dose) and on the morning of Day 15 (trough sample 24 hours post the final Day 14 dose). A volume of approximately 100 µL is collected into tubes, allowed to clot at 2-8° C., centrifuged, and the serum removed from above the clot pellet and stored frozen at −80° C. until ready for concentration measurement.

Example

MTS (Cell Viability) assay. Test compounds are also evaluated in a conventional cytotoxicity assay. Uninfected and stimulated PBMCs are plated in a 96 well flat-bottom plate at 200,000 cells in 200 µL volume of the media in quadruplicates for 3 days at 37° C., in a 5% $CO_2$, humidified incubator. 20 µL of CellTiter 96 AQueous One Solution Reagent (Promega) is added to each well of the plate, and the plate is incubated at 37° C., in a 5% $CO_2$, humidified incubator for 3 h. The plate is then read on a plate reader at 490 nm. The readings are then measured as percentage of viability relative to the control. In each case, test compound did not exhibit cytotoxicity at 5 µM. It is appreciated that the lack of cyctoxicity supports the conclusion that the test compound activity in reducing viral titer is specific to the viral disease.

Example

Micro-Ames Test for Mutagenicity. Compounds described herein are not mutagenic. Compounds described herein and tested in this assay did not show mutagenicity at the highest concentrations tested (as high as 500 µg/plate) in rat liver microsomes.

Example

Mammalian Erythrocyte Micronucleus Test. The clastogenic potential of compounds described herein is evaluated as measured by the ability to induce micronucleated polychromatic erythrocytes in mouse bone marrow. Reportedly, mice, such as male Hsd:ICR (CD-1®) mice, are a standard and accepted rodent species for regulatory toxicology and mutagenicity studies. Also reportedly, oral gavage and intraperitoneal routes of administration are routinely used and are widely-accepted for use in the mammalian bone marrow erythrocyte micronucleus assay. Animals are randomized into group nos. 1 through 10 stratified on the basis of body weight using a computer-generated randomization program. Test compounds and negative control (vehicle) are administered once by intraperitoneal injection. The positive control (cyclophosphamide monohydrate) is administered once by oral gavage. The maximum tolerated doses (MTD), a dose that induces some signs of toxicity, but does not induce mortality within 3 days after administration) is administered. Approximately 24 hours (first 3 mice in the groups 1-9) and 48 hours (remaining mice including the group 10 mice) after dose administration, animals are euthanized by carbon dioxide asphyxiation. Immediately following euthanasia, the femurs are exposed, cut just above the knee and the bone marrow is aspirated into a syringe containing fetal bovine serum and processed. Typically, at least two bone marrow slides are prepared from each animal, air dried, fixed, stained and scored. The slides are stained with May-Gruenwald-Giemsa stain and may be coded by an individual not involved with the scoring process (blinded). Using a light microscope and a medium magnification, an area of acceptable quality is selected such that the cells are well spread and stained. Polychromatic erythrocytes (PCE; 2000/animal; 10,000/dose group) are scored for presence of micronuclei. In the event that evaluation of 2000 PCEs/animal or 10,000 PCEs/group is not possible, the evaluation of the results may be based on the actual number of enumerated cells. The proportion of polychromatic erythrocytes to total erythrocytes (EC) is also recorded per 1000 erythrocytes (PCEs/EC ratio). The proportion of polychromatic erythrocytes to total erythrocytes in test compound-treated animals should not be less than 20% of the control value. In order to quantify the test compound effect on erythropoiesis, as an indicator of bone marrow toxicity, the proportion of polychromatic erythrocytes to total erythrocytes is evaluated for each animal and treatment group. Compounds described herein, tested at 100-300 mg/kg, are not clastogenic and do not cause the induction of micronucleated polychromatic erythrocytes (MPCEs) in bone marrow. Cyclophosphamide monohydrate (positive control) induces a significant increase in the incidence of micronucleated polychromatic erythrocytes at the 48 hour time-point (p≤0.05, Kastenbaum-Bowman Tables) and some cytotoxicity. These results indicate that the bone marrow erythropoietic cells are exposed to cyclophosphamide monohydrate and that this compound, a known clastogenic, induces formation of micronuclei and inhibits erythropoiesis.

Compound Example 1

The following compounds are described herein

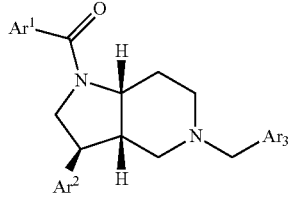

| Example | Ar$^1$ | Ar$^2$ | Ar$^3$ |
|---|---|---|---|
| 1 | Ph | 4-F—C$_6$H$_4$ | 4-F—C$_6$H$_4$ |
| 2 | 3-Pyridyl | 4-F—C$_6$H$_4$ | 4-Cl—C$_6$H$_4$ |
| 3 | Ph | 4-F—C$_6$H$_4$ | 3-MeO—C$_6$H$_4$ |
| 4 | Ph | 4-MeO—C$_6$H$_4$ | 3-F—C$_6$H$_4$ |
| 5 | 2-F—C$_6$H$_4$ | 3-Thienyl | 4-F—C$_6$H$_4$ |
| 6 | Ph | 4-F—C$_6$H$_4$ | 2-F—C$_6$H$_4$ |
| 7 | 2-Thienyl | 4-F—C$_6$H$_4$ | 4-F—C$_6$H$_4$ |
| 8 | Ph | 4-F—C$_6$H$_4$ | Ph |
| 9 | Ph | 4-F—C$_6$H$_4$ | 4-MeO—C$_6$H$_4$ |
| 10 | Ph | 4-MeO—C$_6$H$_4$ | 2-F—C$_6$H$_4$ |
| 11 | 2-F—C$_6$H$_4$ | 3-Thienyl | 3-Me—C$_6$H$_4$ |
| 12 | 2-F—C$_6$H$_4$ | 3-Thienyl | 3-F—C$_6$H$_4$ |
| 13 | Ph | 3-MeO—C$_6$H$_4$ | 3-Thienyl |
| 14 | 3-Pyridyl | 4-F—C$_6$H$_4$ | Ph |
| 15 | 2-Thienyl | 4-F—C$_6$H$_4$ | 2-F—C$_6$H$_4$ |
| 16 | 2-Thienyl | 4-F—C$_6$H$_4$ | 3-F—C$_6$H$_4$ |
| 17 | Ph | 3-MeO—C$_6$H$_4$ | 2-F—C$_6$H$_4$ |
| 18 | Ph | 3-MeO—C$_6$H$_4$ | 4-F—C$_6$H$_4$ |
| 19 | 2-F—C$_6$H$_4$ | 3-Thienyl | 3-Thienyl |
| 20 | Ph | 3-MeO—C$_6$H$_4$ | 2-Me—C$_6$H$_4$ |
| 21 | Ph | 3-MeO—C$_6$H$_4$ | 4-Me—C$_6$H$_4$ |
| 22 | 3-Pyridyl | 4-F—C$_6$H$_4$ | 3-Me—C$_6$H$_4$ |
| 23 | 2-Pyridyl | 4-F—C$_6$H$_4$ | 4-Cl—C$_6$H$_4$ |
| 24 | 3-Pyridyl | 4-F—C$_6$H$_4$ | 4-MeO—C$_6$H$_4$ |
| 25 | Ph | 4-MeO—C$_6$H$_4$ | Ph |
| 26 | 2-Pyridyl | 4-F—C$_6$H$_4$ | 4-MeO—C$_6$H$_4$ |
| 27 | 2-Pyridyl | 4-F—C$_6$H$_4$ | 3-MeO—C$_6$H$_4$ |
| 28 | Ph | 4-MeO—C$_6$H$_4$ | 2-Thienyl |
| 29 | 2-Pyridyl | 4-F—C$_6$H$_4$ | 2-F—C$_6$H$_4$ |
| 30 | Ph | 3-MeO—C$_6$H$_4$ | 3-F—C$_6$H$_4$ |
| 31 | Ph | 3-Thienyl | 2-Thienyl |
| 32 | Ph | 3-Thienyl | 3-Thienyl |
| 33 | 4-Pyridyl | 3-Thienyl | 2-Thienyl |
| 34 | 4-Pyridyl | 3-Thienyl | 3-Thienyl |
| 35 | 2-F—C$_6$H$_4$ | 3-Thienyl | Ph |
| 36 | 2-F—C$_6$H$_4$ | 3-Thienyl | 2-F—C$_6$H$_4$ |
| 37 | 2-F—C$_6$H$_4$ | 3-Thienyl | 2-Thienyl |
| 38 | 2-F—C$_6$H$_4$ | 3-Thienyl | 4-Me—C$_6$H$_4$ |
| 39 | 2-F—C$_6$H$_4$ | 3-Thienyl | 4-Pyridyl |
| 40 | 2-F—C$_6$H$_4$ | 3-Thienyl | 3-Pyridyl |
| 41 | 2-F—C$_6$H$_4$ | 3-Thienyl | 2-Pyridyl |
| 42 | 4-F—C$_6$H$_4$ | 3-Thienyl | 2-Thienyl |
| 43 | Ph | 3-MeO—C$_6$H$_4$ | Ph |
| 44 | Ph | 3-MeO—C$_6$H$_4$ | 2-Thienyl |
| 45 | Ph | 3-MeO—C$_6$H$_4$ | 4-Pyridyl |
| 46 | Ph | 3-MeO—C$_6$H$_4$ | 3-Pyridyl |
| 47 | Ph | 3-MeO—C$_6$H$_4$ | 2-Pyridyl |
| 48 | 3-Pyridyl | 4-F—C$_6$H$_4$ | 2-Me—C$_6$H$_4$ |
| 49 | 3-Pyridyl | 4-F—C$_6$H$_4$ | 3-Pyridyl |
| 50 | 2-Pyridyl | 4-F—C$_6$H$_4$ | Ph |
| 51 | 2-Pyridyl | 4-F—C$_6$H$_4$ | 3-Pyridyl |
| 52 | 2-Pyridyl | 4-F—C$_6$H$_4$ | 2-Pyridyl |
| 53 | 2-Pyridyl | 4-F—C$_6$H$_4$ | 3-Me—C$_6$H$_4$ |
| 54 | 2-Thienyl | 4-F—C$_6$H$_4$ | Ph |
| 55 | 2-Thienyl | 4-F—C$_6$H$_4$ | 3-Pyridyl |
| 56 | 2-Thienyl | 4-F—C$_6$H$_4$ | 2-Pyridyl |
| 57 | 2-Thienyl | 4-F—C$_6$H$_4$ | 2-Me—C$_6$H$_4$ |
| 58 | Ph | 4-MeO—C$_6$H$_4$ | 2-Pyridyl |
| 59 | Ph | 4-MeO—C$_6$H$_4$ | 3-Thienyl |
| 60 | 3-Pyridyl | 4-F—C$_6$H$_4$ | 2-F—C$_6$H$_4$ |
| 61 | 3-Pyridyl | 4-F—C$_6$H$_4$ | 4-F—C$_6$H$_4$ |
| 62 | 3-Pyridyl | 4-F—C$_6$H$_4$ | 2-Cl—C$_6$H$_4$ |
| 63 | 3-Pyridyl | 4-F—C$_6$H$_4$ | 2-Thienyl |
| 64 | 3-Pyridyl | 4-F—C$_6$H$_4$ | 4-Pyridyl |

-continued

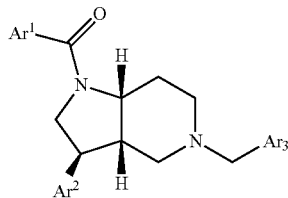

| Example | Ar¹ | Ar² | Ar³ |
|---|---|---|---|
| 65 | 3-Pyridyl | 4-F—C₆H₄ | 3-Thienyl |
| 66 | 4-Pyridyl | 4-F—C₆H₄ | 4-MeO—C₆H₄ |
| 67 | 4-Pyridyl | 4-F—C₆H₄ | 2-Thienyl |
| 68 | 4-Pyridyl | 4-F—C₆H₄ | 3-Thienyl |

Compound Example 2

The following compounds are described herein:

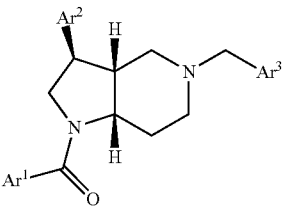

| Example | Ar¹ | Ar² | Ar³ |
|---|---|---|---|
| 101 | Ph | 4-MeO—C₆H₄ | 4-F—C₆H₄ |
| 102 | 4-Pyridyl | 4-F—C₆H₄ | 2-Cl—C₆H₄ |
| 103 | Ph | 3-Thienyl | 2-F—C₆H₄ |
| 104 | Ph | 4-F—C₆H₄ | 3-F—C₆H₄ |
| 105 | Ph | 3-Thienyl | Ph |
| 106 | Ph | 3-Thienyl | 4-F—C₆H₄ |
| 107 | Ph | 3-Thienyl | 4-Cl—C₆H₄ |
| 108 | Ph | 3-Thienyl | 3,4-F₂—C₆H₃ |
| 109 | 3-Pyridyl | 4-F—C₆H₄ | 2-MeO—C₆H₄ |
| 110 | 4-Pyridyl | 4-F—C₆H₄ | 3-Me—C₆H₄ |
| 111 | Ph | 4-F—C₆H₄ | 1-Me-pyrazol-4-yl |
| 112 | Ph | 4-F—C₆H₄ | 1,5-Me₂-pyrazol-4-yl |
| 113 | Ph | 4-F—C₆H₄ | 1,3-Me₂-pyrazol-4-yl |
| 114 | Ph | 3-Thienyl | 4-MeO—C₆H₄ |
| 115 | 4-Pyridyl | 3-Thienyl | 4-F—C₆H₄ |
| 116 | 4-Pyridyl | 3-Thienyl | 4-Cl—C₆H₄ |
| 117 | 4-Pyridyl | 3-Thienyl | 3-Cl—C₆H₄ |
| 118 | 4-Pyridyl | 3-Thienyl | 3,4-F₂—C₆H₃ |
| 119 | 4-F—C₆H₄ | 3-Thienyl | Ph |
| 120 | 4-F—C₆H₄ | 3-Thienyl | 4-F—C₆H₄ |
| 121 | 3-Pyridyl | 4-F—C₆H₄ | 3-MeO—C₆H₄ |
| 122 | 4-Pyridyl | 4-F—C₆H₄ | 2-MeO—C₆H₄ |
| 123 | 2-Pyridyl | 4-F—C₆H₄ | 2-Cl—C₆H₄ |
| 124 | 4-Pyridyl | 4-F—C₆H₄ | 4-F—C₆H₄ |
| 125 | 2-Pyridyl | 4-F—C₆H₄ | 4-F—C₆H₄ |
| 126 | 2-Pyridyl | 4-F—C₆H₄ | 3-F—C₆H₄ |
| 127 | Ph | 3-Thienyl | 2-Cl—C₆H₄ |
| 128 | Ph | 3-Thienyl | 3-Pyridyl |
| 129 | Ph | 3-Thienyl | 3-MeO—C₆H₄ |
| 130 | Ph | 3-Thienyl | 2-MeO—C₆H₄ |
| 131 | Ph | 3-Thienyl | 3-Cl—C₆H₄ |
| 132 | Ph | 3-Thienyl | 2-Me—C₆H₄ |
| 133 | Ph | 3-Thienyl | 3-Me—C₆H₄ |
| 134 | Ph | 3-Thienyl | 3-F—C₆H₄ |
| 135 | Ph | 3-Thienyl | 2,3-F₂—C₆H₃ |
| 136 | 4-Pyridyl | 3-Thienyl | Ph |
| 137 | 4-Pyridyl | 3-Thienyl | 2-F—C₆H₄ |
| 138 | 4-Pyridyl | 3-Thienyl | 2-Cl—C₆H₄ |
| 139 | 4-Pyridyl | 3-Thienyl | 4-MeO—C₆H₄ |
| 140 | 4-Pyridyl | 3-Thienyl | 4-Me—C₆H₄ |
| 141 | 4-Pyridyl | 3-Thienyl | 4-i-Pr—C₆H₄ |

-continued

| Example | Ar¹ | Ar² | Ar³ |
|---|---|---|---|
| 142 | 4-Pyridyl | 3-Thienyl | 3-MeO—C₆H₄ |
| 143 | 4-Pyridyl | 3-Thienyl | 2-MeO—C₆H₄ |
| 144 | 4-Pyridyl | 3-Thienyl | 2-Me—C₆H₄ |
| 145 | 4-Pyridyl | 3-Thienyl | 2,3-F₂—C₆H₄ |
| 146 | 4-F—C₆H₄ | 3-Thienyl | 2-F—C₆H₄ |
| 147 | 4-F—C₆H₄ | 3-Thienyl | 4-Me—C₆H₄ |
| 148 | 4-F—C₆H₄ | 3-Thienyl | 4-Pyridyl |
| 149 | 4-F—C₆H₄ | 3-Thienyl | 3-Pyridyl |
| 150 | 4-F—C₆H₄ | 3-Thienyl | 2-Pyridyl |
| 151 | 4-F—C₆H₄ | 3-Thienyl | 2-Me—C₆H₄ |
| 152 | 4-F—C₆H₄ | 3-Thienyl | 3-Me—C₆H₄ |
| 153 | 4-F—C₆H₄ | 3-Thienyl | 3-F—C₆H₄ |
| 154 | 2-Pyridyl | 4-F—C₆H₄ | 2-Me—C₆H₄ |
| 155 | 3-Pyridyl | 4-F—C₆H₄ | 3-Pyridyl |
| 156 | 3-Pyridyl | 4-F—C₆H₄ | 2-Pyridyl |
| 157 | 3-Pyridyl | 4-F—C₆H₄ | 3-F—C₆H₄ |
| 158 | 3-Pyridyl | 4-F—C₆H₄ | 1,5-Me₂-pyrazol-4-yl |
| 159 | 3-Pyridyl | 4-F—C₆H₄ | 1,3-Me₂-pyrazol-4-yl |
| 160 | 4-Pyridyl | 4-F—C₆H₄ | Ph |
| 161 | 4-Pyridyl | 4-F—C₆H₄ | 2-F—C₆H₄ |
| 162 | 4-Pyridyl | 4-F—C₆H₄ | 4-Pyridyl |
| 163 | 4-Pyridyl | 4-F—C₆H₄ | 3-MeO—C₆H₄ |
| 164 | 4-Pyridyl | 4-F—C₆H₄ | 2-Pyridyl |
| 165 | 4-Pyridyl | 4-F—C₆H₄ | 2-Me—C₆H₄ |
| 166 | 4-Pyridyl | 4-F—C₆H₄ | 3-F—C₆H₄ |

The following publications, and each additional publication cited herein, are incorporated herein by reference.

1. Sepkowitz K A (2001). "AIDS—the first 20 years". N. Engl. J. Med. 344 (23): 1764-72
2. Weiss R A (1993). "How does HIV cause AIDS?" Science 260 (5112): 1273-9
3. Dybul M, Fauci A S, Bartlett J G, Kaplan J E, Pau A K; Panel on Clinical Practices for Treatment of HIV. (2002). "Guidelines for using antiretroviral agents among HIV-infected adults and adolescents". Ann. Intern. Med. 137 (5 Pt 2): 381-433.
4. Martinez-Picado J, DePasquale M P, Kartsonis N, et al. (2000). "Antiretroviral resistance during successful therapy of human immunodeficiency virus type 1 infection". Proc. Natl. Acad. Sci. U.S.A. 97 (20): 10948-10953.
5. Cory A H, Owen T C, Barltrop J A, Cory J G (1991). "Use of an aqueous soluble tetrazolium/formazan assay for cell growth assays in culture". Cancer Commun. 3 (7): 207-212. ISSN 0955-3541. PMID 1867954.
6. Hashida S, Hashinaka K, Ishikawa S, Ishikawa E. (1997). "More reliable diagnosis of infection with human immunodeficiency virus type 1 (HIV-1) by detection of antibody IgGs to pol and gag proteins of HIV-1 and p24 antigen of HIV-1 in urine, saliva, and/or serum with highly sensitive and specific enzyme immunoassay (immune complex transfer enzyme immunoassay)." J Clin Lab Anal. 1997; (5):267-86. Erratum in: J Clin Lab Anal 1998; (1):76.

What is claimed is:

1. A method for treating a host animal with HIV, the method comprising the step of administering to the host animal a pharmaceutical composition comprising a therapeutically effective amount of one or more compounds of the formula

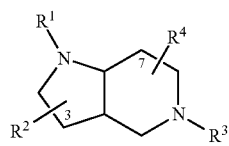

or a pharmaceutically acceptable salt thereof, wherein:

$R^1$ is arylcarbonyl, wherein aryl is monocyclic and is optionally substituted with halo or alkyl;

$R^2$ is aryl, wherein aryl is monocyclic and is optionally substituted with halo, alkyl, or alkoxyl, and wherein $R^2$ is at C-3;

$R^3$ is arylmethyl, wherein aryl is monocyclic and is optionally substituted with halo, alkyl, or alkoxyl; and $R^4$ is hydrogen;

wherein the pharmaceutical composition optionally comprises one or more pharmaceutically acceptable carriers, diluent, or excipients, or combinations thereof.

2. The method of claim 1 wherein the stereochemistry of the ring fusion in the compound is syn.

3. The method of claim 1 wherein the compound is of the formula

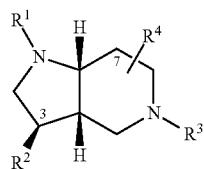

or a pharmaceutically acceptable salt thereof.

4. The method of claim 1 wherein $R^1$ is optionally substituted benzoyl.

5. The method of claim 1 wherein $R^1$ is benzoyl.

6. The method of claim 1 wherein $R^1$ is picolinoyl.

7. The method of claim 1 wherein $R^1$ is 3-picolinoyl.

8. The method of claim 1 wherein $R^2$ is optionally substituted phenyl.

9. The method of claim 1 wherein $R^2$ is phenyl substituted with halo, alkoxy, or a combination thereof.

10. The method of claim 1 wherein $R^2$ is halophenyl.

11. The method of claim 1 wherein $R^2$ is alkoxyphenyl.

12. The method of claim 1 wherein $R^2$ is methoxyphenyl.

13. The method of claim 1 wherein $R^3$ is optionally substituted benzyl.

14. The method of claim 1 wherein $R^3$ is halo substituted benzyl.

15. The method of claim 1 wherein $R^3$ is fluorobenzyl or chlorobenzyl.

16. The method of claim 1 wherein the compound is of the formula

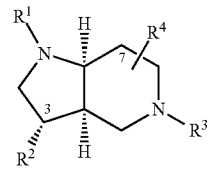

or a pharmaceutically acceptable salt thereof.

17. The method of claim 1 wherein the compound is of the formula

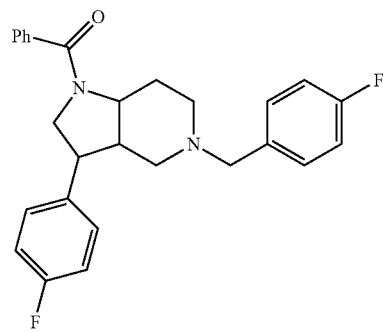 [SMILES: O=C(c1ccccc1)N1CC(c2ccc(F)cc2)C2CN(Cc3ccc(F)cc3)CCC21]

or a pharmaceutically acceptable salt thereof.

18. The method of claim 1 wherein the compound is of the formula

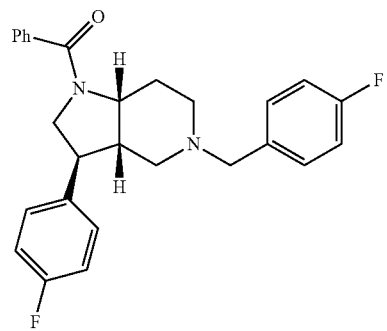 [SMILES: O=C(c1ccccc1)N1C[C@H](c2ccc(F)cc2)[C@H]2CN(Cc3ccc(F)cc3)CC[C@H]21]

or a pharmaceutically acceptable salt thereof.

19. The method of claim 1 wherein the compound is of the formula

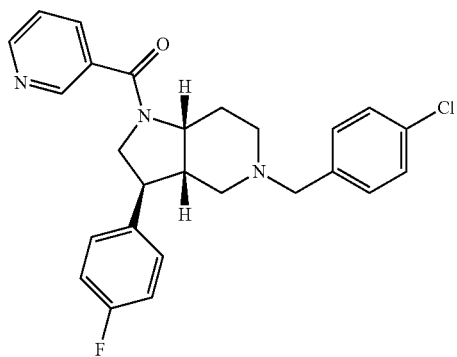 [SMILES: O=C(c1cccnc1)N1C[C@H](c2ccc(F)cc2)[C@H]2CN(Cc3ccc(Cl)cc3)CC[C@H]21]

or a pharmaceutically acceptable salt thereof.

20. The method of claim 1 wherein the compound is of the formula

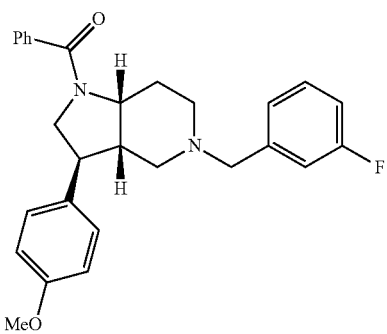 [SMILES: COc1ccc([C@H]2CN(C(=O)c3ccccc3)[C@@H]3CCN(Cc4cccc(F)c4)C[C@H]23)cc1]

or a pharmaceutically acceptable salt thereof.

21. The method of claim 1 wherein the compound is of the formula

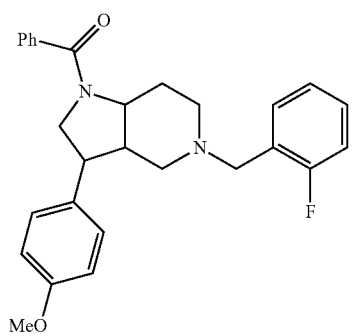 [SMILES: COc1ccc(C2CN(C(=O)c3ccccc3)C3CCN(Cc4ccccc4F)CC23)cc1]

or a pharmaceutically acceptable salt thereof.

22. The method of claim 1 wherein the compound is of the formula

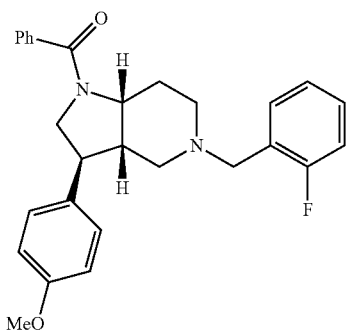 [SMILES: COc1ccc([C@H]2CN(C(=O)c3ccccc3)[C@@H]3CCN(Cc4ccccc4F)C[C@H]23)cc1]

or a pharmaceutically acceptable salt thereof.

23. The method of claim 1 wherein the compound is of the formula

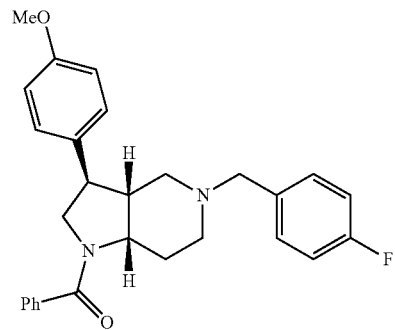 [SMILES: COc1ccc([C@@H]2CN(C(=O)c3ccccc3)[C@H]3CCN(Cc4ccc(F)cc4)C[C@@H]23)cc1]

or a pharmaceutically acceptable salt thereof.

24. The method of claim 1 wherein the pharmaceutical composition is administered in combination with a second HIV infection-treating agent.

* * * * *